(12) United States Patent
Michlitsch

(10) Patent No.: US 8,323,311 B2
(45) Date of Patent: Dec. 4, 2012

(54) AUTOLOGOUS WOUND SEALING APPARATUS

(75) Inventor: Kenneth J. Michlitsch, Livermore, CA (US)

(73) Assignee: Abbott Laboratories Vascular Enterprises Limited, Dublin (IE)

( * ) Notice: Subject to any disclaimer, the term of this patent is extended or adjusted under 35 U.S.C. 154(b) by 158 days.

(21) Appl. No.: 12/853,139

(22) Filed: Aug. 9, 2010

(65) Prior Publication Data

US 2010/0305608 A1 Dec. 2, 2010

Related U.S. Application Data

(63) Continuation of application No. 10/523,219, filed as application No. PCT/EP03/08246 on Jul. 25, 2003, now Pat. No. 7,771,454.

(60) Provisional application No. 60/401,226, filed on Aug. 1, 2002.

(51) Int. Cl.
*A61B 17/08* (2006.01)
(52) U.S. Cl. ...................................................... 606/213
(58) Field of Classification Search .................. 606/139, 606/148, 191, 194, 213–215, 232; 604/15
See application file for complete search history.

(56) References Cited

U.S. PATENT DOCUMENTS

| | | | |
|---|---|---|---|
| 4,890,612 A * | 1/1990 | Kensey | 606/213 |
| 5,061,274 A | 10/1991 | Kensey | |
| 5,382,230 A * | 1/1995 | Bonn | 604/32 |
| 5,425,744 A | 6/1995 | Fagan et al. | |
| 5,486,195 A * | 1/1996 | Myers et al. | 606/213 |
| 5,545,178 A | 8/1996 | Kensey et al. | |
| 5,626,601 A | 5/1997 | Gershony et al. | |
| 5,649,959 A | 7/1997 | Hannam et al. | |
| 6,159,232 A | 12/2000 | Nowakowski | |
| 6,162,192 A | 12/2000 | Cragg et al. | |
| 6,391,037 B1 | 5/2002 | Greenhalgh | |
| 7,771,454 B2 | 8/2010 | Michlitsch | |
| 2002/0072767 A1 | 6/2002 | Zhu | |

FOREIGN PATENT DOCUMENTS

| | | |
|---|---|---|
| EP | 1159982 | 12/2001 |
| WO | WO96/24290 | 8/1996 |
| WO | WO 2004/012602 | 2/2004 |

OTHER PUBLICATIONS

U.S. Appl. No. 60/401,226, filed Aug. 1, 2002, Michlitsch.
U.S. Appl. No. 10/523,219, Mail Date Jul. 11, 2006, Office Action.

(Continued)

*Primary Examiner* — Corrine M McDermott
*Assistant Examiner* — Gregory Anderson
(74) *Attorney, Agent, or Firm* — Workman Nydegger; Jonathan D. Feuchtwang

(57) ABSTRACT

The apparatus is provided for sealing a vascular puncture tract by forming the autologous plug within the puncture tract, and extruding that plug into the puncture tract. The apparatus of the present invention forms an autologous blood plug by drawing blood into the apparatus from a vessel, mixing a blood congealing agent with the drawn blood, and ejecting a plug formed from the clotted blood within the puncture tract. Also provided are various closure elements to isolate the drawn blood from the vessel during mixture with the blood congealing agent, and to facilitate placement of the apparatus relative to the vessel.

20 Claims, 18 Drawing Sheets

OTHER PUBLICATIONS

U.S. Appl. No. 10/523,219, Mail Date Sep. 5, 2006, Office Action.
U.S. Appl. No. 10/523,219, Mail Date Jan. 4, 2007, Office Action.
U.S. Appl. No. 10/523,219, Mail Date Mar. 28, 2007, Office Action.
U.S. Appl. No. 10/523,219, Mail Date Jul. 24, 2007, Office Action.
U.S. Appl. No. 10/523,219, Mail Date Nov. 21, 2007, Office Action.
U.S. Appl. No. 10/523,219, Mail Date Sep. 17, 2008, Office Action.
U.S. Appl. No. 10/523,219, Mail Date Apr. 14, 2009, Office Action.
U.S. Appl. No. 10/523,219, Mail Date Apr. 2, 2010, Notice of Allowance.
U.S. Appl. No. 10/523,219, Mail Date Jul. 21, 2010, Issue Notification.

* cited by examiner

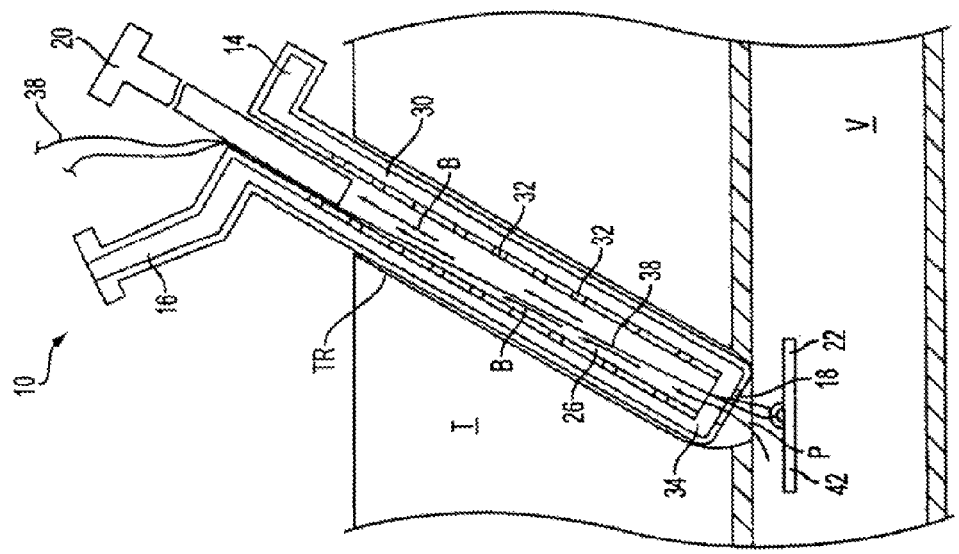
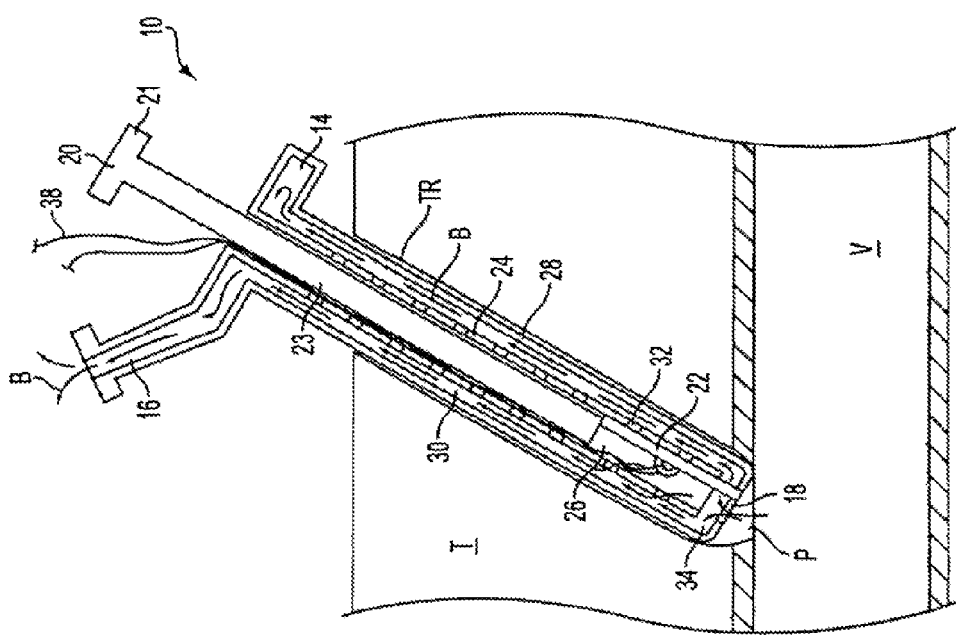

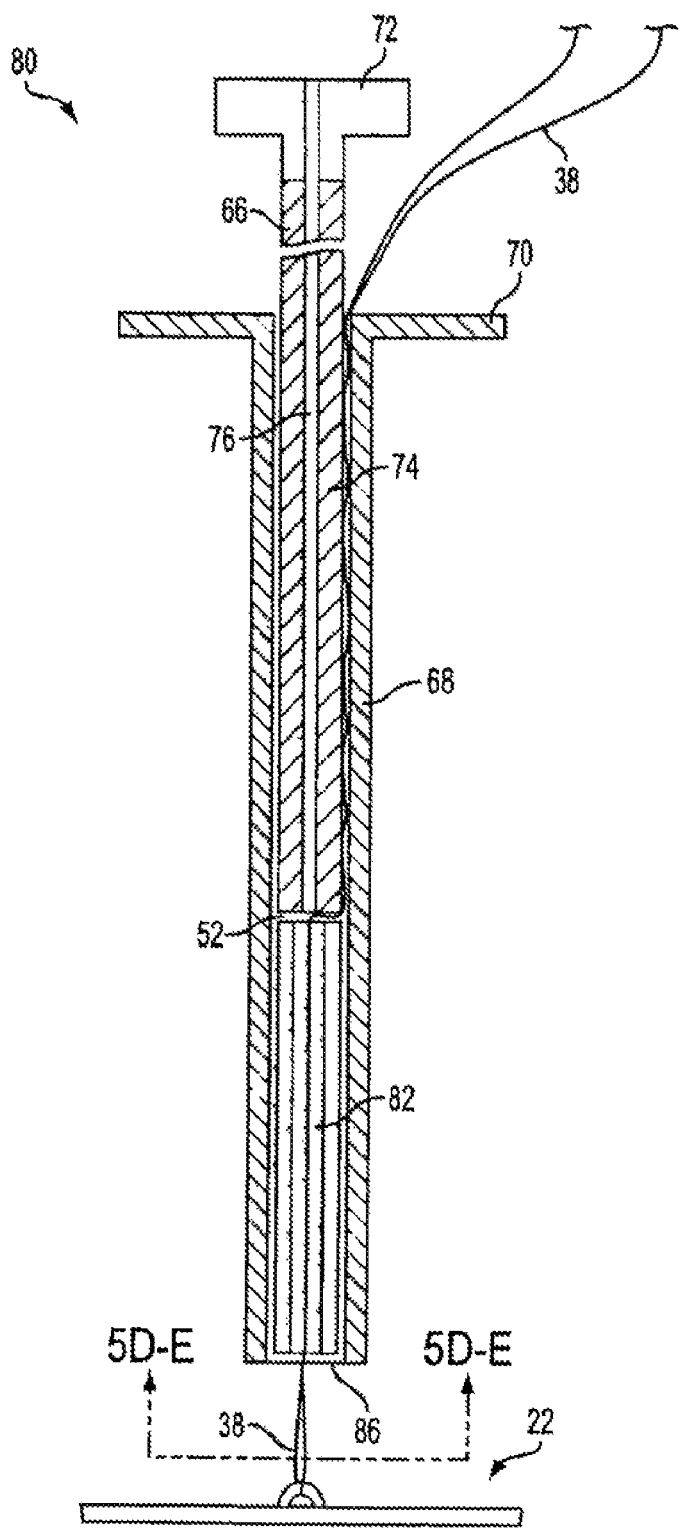
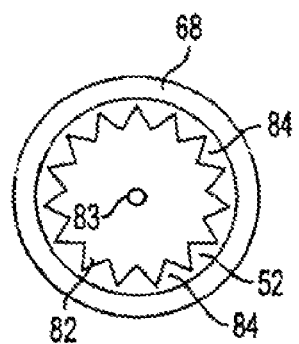
FIG. 5D
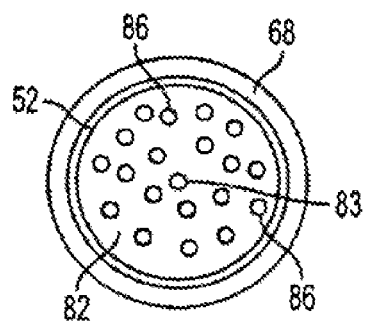
FIG. 5E
FIG. 5C

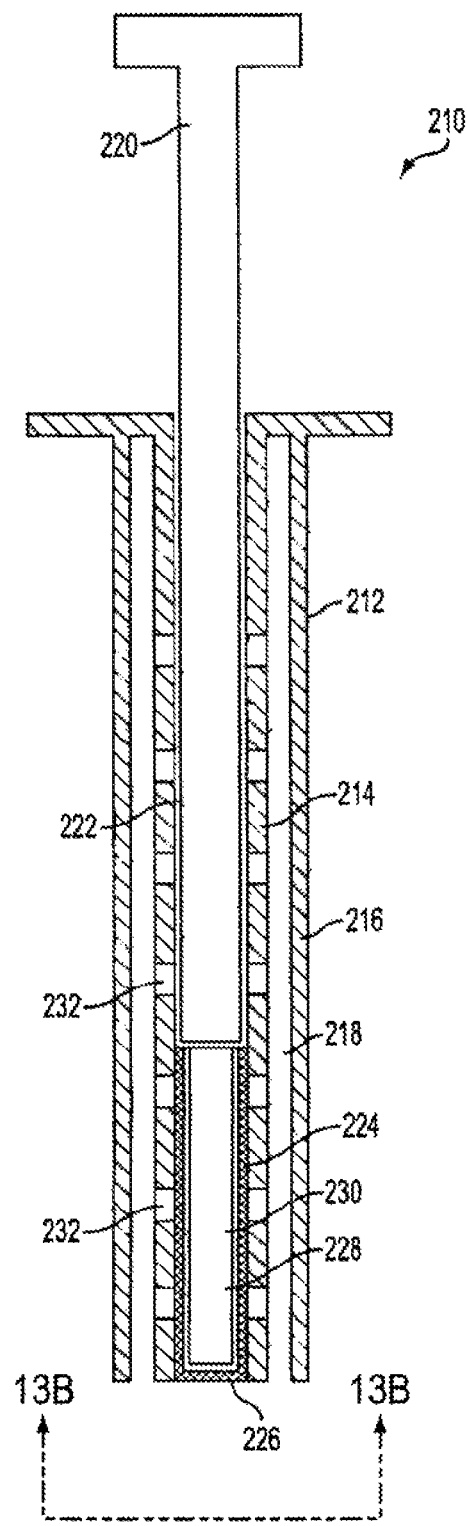
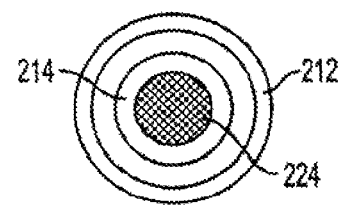
FIG. 13B
FIG. 13A

AUTOLOGOUS WOUND SEALING APPARATUS

CROSS-REFERENCE TO RELATED APPLICATIONS

This is a continuation application of U.S. patent application Ser. No. 10/523,219, now U.S. Pat. No. 7,771,454, filed 19 Oct. 2005, which is a 371 Nationalization of PCT/EP2003/008246, filed 25 Jul. 2003, which claims the benefit of and priority to U.S. Provisional Patent Application Ser. No. 60/401,226, filed 1 Aug. 2002, the disclosures of which are incorporated herein by this reference.

BACKGROUND OF THE INVENTION

1. The Field of the Invention

The present invention relates to apparatus for sealing puncture tracts. More specifically, the invention relates to apparatus that seals a puncture tract by forming and extruding an autologous plug therein.

2. The Background of the Invention

A large number of medical diagnostic and therapeutic procedures involve the percutaneous introduction of instrumentation into the blood vessel. For example, coronary angioplasty, angiography, atherectomy, stenting, and numerous other procedures often involve accessing the vasculature through placement of a catheter or other device in a patient's femoral artery or other blood vessel. Once the procedure is completed and the catheter or other diagnostic or therapeutic device is removed, bleeding from the resultant vascular puncture must be stopped.

Traditionally, a medical practitioner applies external pressure to the puncture site to stem bleeding until hemostasis occurs (i.e. when the clotting and tissue rebuilding have sealed the puncture). This method, however, presents numerous problems. In some instances, this pressure must be applied for up to an hour or more, during which time the patient is uncomfortably immobilized. In addition, there exists a risk of hematoma since bleeding from the puncture may continue until sufficient clotting occurs, particularly if the patient moves during the clotting process. Furthermore, application of external pressure to stop bleeding may be unsuitable for patients with substantial amounts of subcutaneous adipose tissue since the skin surface may be a considerable distance from the puncture site, thereby rendering external compression less effective.

Another traditional approach to subcutaneous puncture closure comprises having a medical practitioner internally suture the vessel puncture. This method, however, often requires a complex procedure and requires considerable skill by the medical practitioner.

Mechanical occlusion devices have been proposed for sealing, e.g., atrial septal defects, and typically comprise two expandable disks that sealingly compress tissue surrounding the hole. One such device is described in U.S. Pat. No. 5,425,744 to Fagan et al. A significant drawback to the Fagan device is that, when deployed into a vessel, the device may protrude into the blood stream, thereby disturbing blood flow and causing thrombosis in the vessel.

Apparatus and methods also are known in which a plug is introduced into the vessel puncture, to cover the puncture and promote hemostasis. Various types of plugs have been proposed. One example is described in U.S. Pat. No. 5,061,274 to Kensey, comprising a plug made from animal-derived collagen. Such apparatus may be unsuitable for some patients due to an adverse immunological reaction to animal-derived collagen, which could lead to anaphylactic shock.

U.S. Pat. No. 6,159,232 to Nowakowski describes an apparatus substantially disposed outside a patient's body that activates a clotting cascade within blood, and then introduces the treated blood to the wound site to complete clotting and promote hemostasis. Disadvantageously, the apparatus described in that patent comprises a multiplicity of primarily standard, off-the-shelf components that a medical practitioner would have to assemble prior to use. This greatly is complicates the procedure, and increases opportunities for human error and contamination. Furthermore, the apparatus resulting from the assembly of the numerous individual components may be unwieldy to use and expensive.

In view of these drawbacks, it would be desirable to provide apparatus for sealing a puncture tract by forming and extruding an autologous plug within the puncture tract.

It also would be desirable to provide apparatus for sealing a puncture tract that are easy to use, and decrease opportunities for error and contamination.

It further would be desirable to provide apparatus for sealing a puncture tract that facilitate placement of the apparatus relative to a vessel.

It still further would be desirable to provide apparatus for sealing a puncture tract that prevent leakage of blood congealing agents into a vessel during delivery thereof.

BRIEF SUMMARY OF THE INVENTION

In view of the foregoing, it is an object of the present invention to provide apparatus for sealing a puncture tract by forming and extruding an autologous plug within the puncture tract.

It also is an object of the present invention to provide apparatus for sealing a puncture tract that are easy to use, and decrease opportunities for error and contamination.

It further is an object of the present invention to provide apparatus for sealing a puncture tract that facilitate placement of the apparatus relative to a vessel.

It even further is an object of the present invention to provide apparatus for sealing a puncture tract that prevent leakage of blood congealing agents into a vessel during delivery thereof.

These and other objects of the present invention are accomplished by providing apparatus for sealing a puncture tract by forming and extruding an autologous plug within the puncture tract. More specifically, the apparatus of the present invention forms the autologous plug by drawing blood into the apparatus from a vessel in fluid communication with the puncture tract, and supplying a blood congealing agent to the drawn blood. Consequently, a plug of clotted blood forms within the apparatus, which then may be extruded out of the apparatus and disposed along at least a portion of the length of the puncture tract.

In a preferred embodiment, the apparatus of the present invention comprises a housing dimensioned to be inserted at least partially into the puncture tract. The housing comprises inner and outer tubes that define an annular lumen. The inner tube comprises a central lumen in which an autologous plug is formed that is then extruded to occlude the puncture tract. The device also comprises a plunger slidably disposed within the central lumen to facilitate drawing blood from the vessel into the central lumen, and extruding the plug from the central lumen into the puncture tract. In alternative embodiments, the annular lumen and/or the outer tube may be omitted.

To isolate a mixture of blood and blood congealing agent from the vessel during formation of the autologous plug, the device further comprises a closure element, such as a pledget, an iris closure, an alignment closure, or a membrane that is permeable to blood but impermeable to the blood congealing agent.

To initiate clotting of the drawn blood within the central lumen, a blood congealing agent, such as, e.g., thrombin, fibrin or human factor VIII, may be introduced thereto by injection from an external source, or by pre-coating the central lumen. Alternatively, the central lumen may be lined or pre-loaded with a matrix that is preferably biodegradable, e.g., gauze, bio-compatible foam or spun fiber, or platinum or thermo-resistive wires may be disposed within the wall of the inner tube for contact with the blood therein.

Disposition of the autologous plug formed from the coagulated blood into the puncture tract seals the puncture tract and vessel from leakage. The tissue surrounding the puncture tract compressively engages the autologous plug along its length, generating frictional forces that prevent the plug from becoming dislodged into the vessel. These and other objects and features of the present invention will become more fully apparent from the following description and appended claims, or may be learned by the practice of the invention as set forth hereinafter.

BRIEF DESCRIPTION OF THE DRAWINGS

Further features of the present invention, its nature and various advantages will be more apparent from the accompanying drawings and the following detailed description of the preferred embodiments, in which:

FIGS. 4A-4E are schematic side-sectional views describing an exemplary method of using the apparatus of FIGS. 2 and 3;

FIGS. 5A-5E are schematic side-sectional and end views of alternative embodiments of apparatus of the present invention;

FIGS. 13A and 13B are, respectively, a schematic side-sectional view and a schematic end view of yet another alternative embodiment of the apparatus of the present invention.

DETAILED DESCRIPTION OF THE INVENTION

Figure 1:
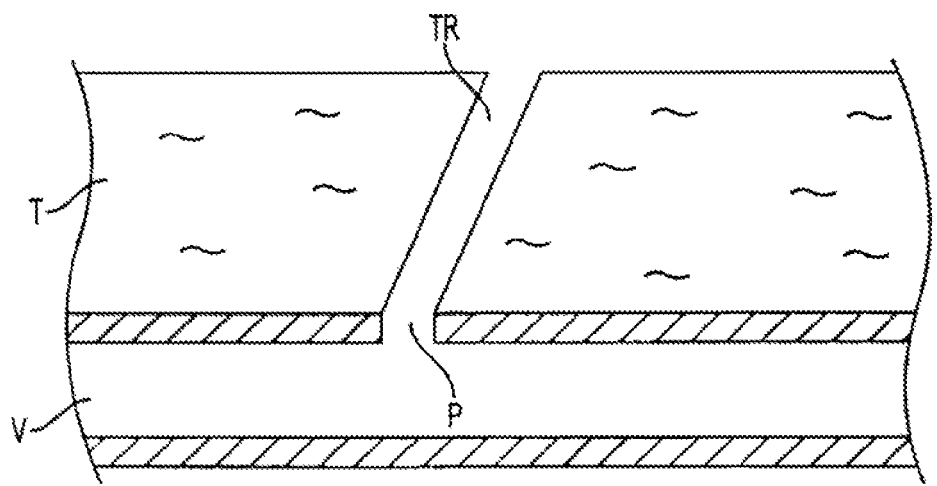
FIG. 1 is a schematic side-sectional view of a vascular puncture tract.

Upon completion of a medical diagnostic or therapeutic procedure involving percutaneous introduction of instrumentation into blood vessel V, removal of the instrumentation from the patient leaves puncture tract TR. As seen in FIG. 1, puncture tract TR extends through subcutaneous tissue T and terminates at puncture P. The apparatus of the present invention is directed to a device for sealing puncture tract TR by facilitating formation and disposition of an autologous plug within the puncture tract. More specifically, the apparatus facilitates formation of the plug by drawing blood into a lumen of the apparatus, and providing a blood congealing agent to the blood therein, which causes the blood to clot and form an autologous plug within the lumen. The autologous plug is extruded from the lumen to seal puncture tract TR, thereby sealing vessel V from blood leakage.

Figure 2:
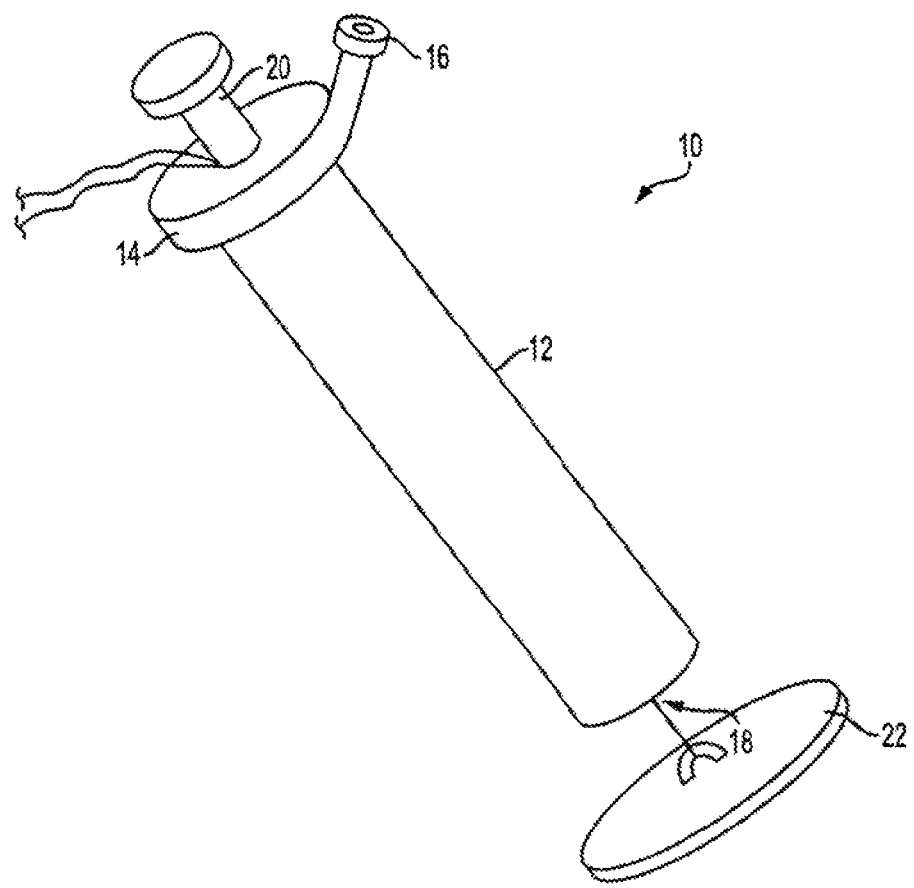
FIG. 2 is a schematic perspective view of is apparatus of the present invention.
Figure 3:
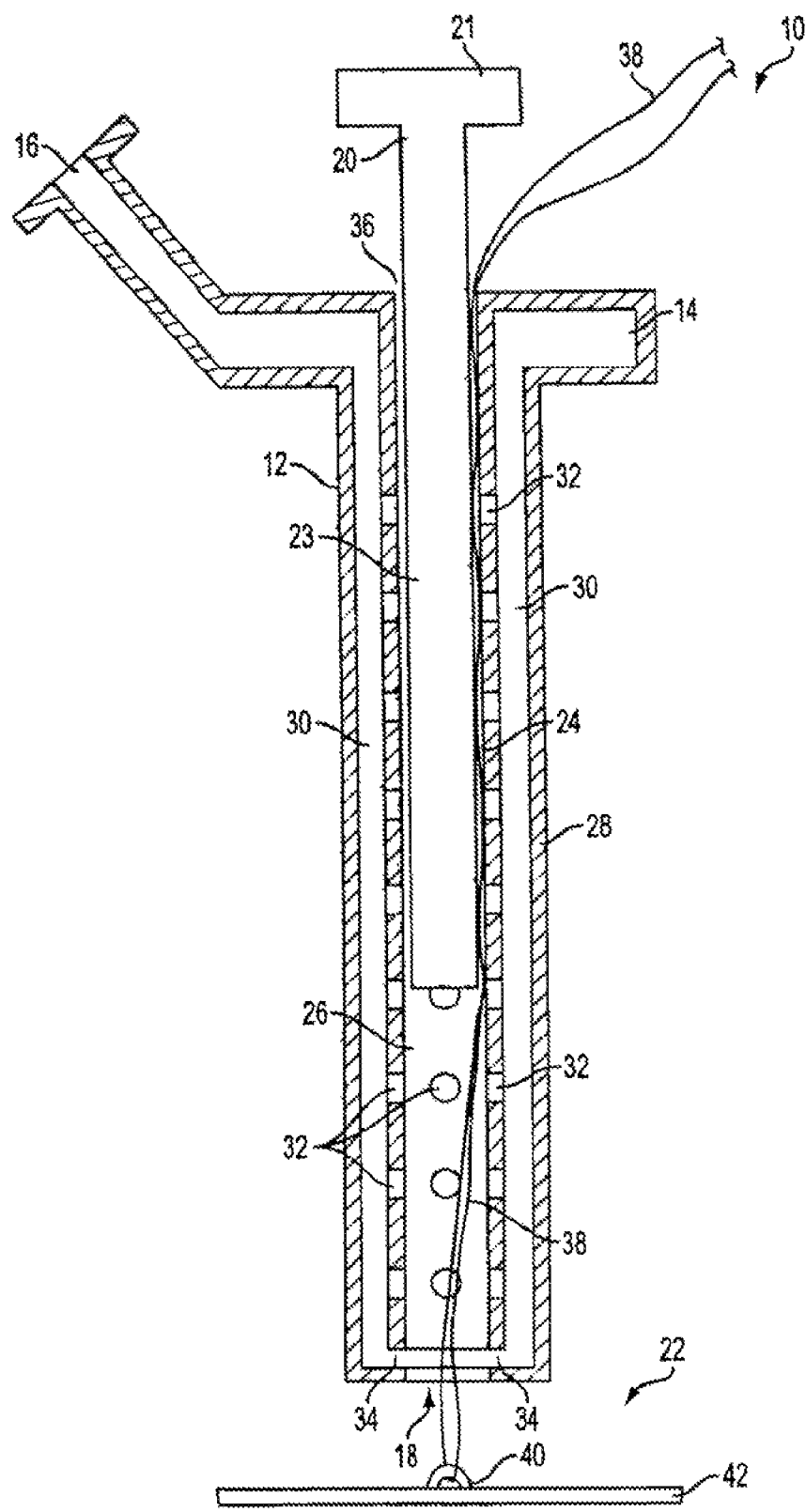
FIG. 3 is a schematic side-sectional view of the apparatus of FIG. 2.

An illustrative embodiment of device 10 of the present invention is shown in FIGS. 2 and 3. Device 10 comprises housing 12 having manifold 14, injection port 16, and distal opening 18, plunger 20 having head 21 and shank 23 disposed for axial translation within housing 12, and pledget 22. Pledget 22 may be disposed within and is removably coupled to housing 12. As described in greater detail hereinbelow, fluid communication between distal opening 18 and injection port 16 permits a medical practitioner to easily determine when device 10 has been advanced is within puncture tract TR to a position just proximal to vessel V.

Housing 12 further comprises inner tube 24 and outer tube 28, which may be distally tapered to provide an atraumatic bumper for advancement of device 10 through puncture tract TR, or may be distally angled for flush alignment with an angled puncture tract TR, such as the puncture tract of FIG. 1. Inner and outer tubes 24 and 28 form annular lumen 30, which is in fluid communication with manifold 14 and injection port 16. Annular lumen 30 extends along the length of inner tube 24 and is in fluid communication with central lumen 26, via plurality of apertures 32. Apertures 32 are disposed through and along the axial length of inner tube 24. Optional gap 34 is defined between the distal ends of inner and outer tubes 24 and 28.

Fluid communication between injection port 16 and central lumen 26 permits a blood congealing agent to be injected through injection port 16, e.g., a luer valve, into blood drawn within central lumen 26. Mixture and chemical interaction between the blood congealing agent, e.g., thrombin, fibrin and/or human factor VIII, and the blood initiates a clotting reaction that congeals the blood into an autologous plug. The plug is extruded from central lumen 26 into puncture tract TR to seal the vessel puncture.

In a preferred embodiment, central lumen 26 has a diameter equal to that of distal opening 18. Once an autologous plug is formed within central lumen 26, it is extruded into puncture tract TR, where the plug engages compliant tissue T surrounding the puncture tract along its length, thereby retaining the plug within the puncture tract. Engagement between the is plug and tissue may be increased by enlarging the diameter of central lumen 26 and distal opening 18, thereby permitting an increase in the diameter and surface area of the autologous plug that is formed and extruded. The diameter of shank 23 of plunger 20 is selected so that shank 23 may be translated within central lumen 26, yet prevents blood leakage around proximal opening 36 of central lumen 26.

As shown in FIGS. 2 and 3, the diameter of central lumen 26 also is dimensioned to permit thread 38 to be translatably disposed between plunger 20 and inner tube 24. Alternatively, plunger 20 may be provided with a thread lumen (not shown) through which thread 38 may be translatably disposed. Thread 38 exits housing 12 through proximal opening 36, and is distally attached to loop 40 of pledget 22. Pledget 22 includes disk 42, to which loop 40 is coupled, preferably rigidly.

In a preferred embodiment, disk 42 is elliptically shaped, and has major and minor axes that permit disk 42 to completely cover puncture P when disposed therein. Accordingly, when pledget 22 is engaged to the inner wall of vessel V within puncture p, immediate hemostasis may be achieved. If the minor axis of disk 42 is greater than the diameter of central lumen 26, disk 42 may be made of a material that permits disk 42 to be elastically deformed to fit within central lumen 26 during delivery of the pledget to vessel V. Once ejected from central lumen 26, disk 42 elastically recovers its elliptical shape. Of course, in addition to elliptical shapes, it will be evident to one of ordinary skill in the art that disk 42 may comprise other shapes, e.g., circular or oblong, so long as disk 42 can completely occlude puncture P when disposed therein.

In accordance with one aspect of the present invention, pledget 22 and thread 38 are made of biodegradable materials, e.g., polyglycolic acid. This permits pledget 22 and thread 38 to be resorbed and excreted from the body along with resorption of the autologous plug, after puncture P and tract TR have healed. It will be evident to one of ordinary skill in the art that, by controlling parameters such as the degree of polymerization and crystallization, the biodegradable material may be engineered to comprise properties that permit disk 42 to elastically deform when inserted into central lumen 26 during delivery, and to degrade at a predetermined rate.

Figure 4D:
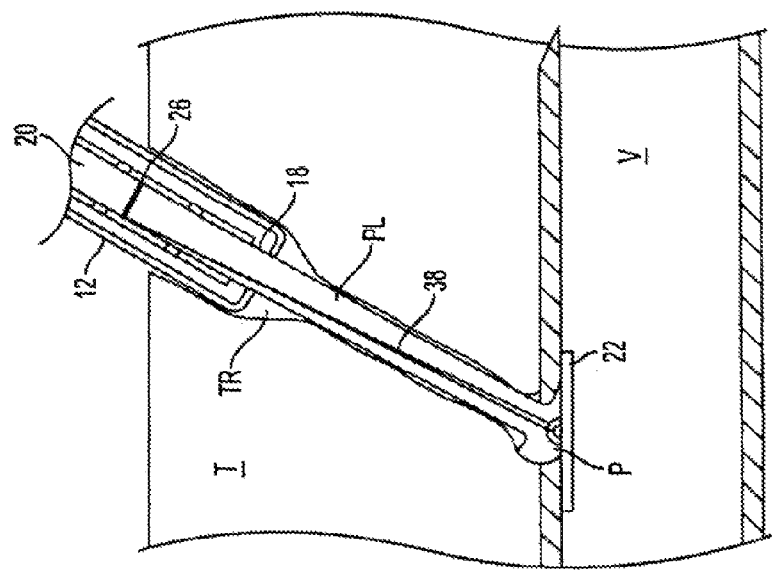
Figure 4C:
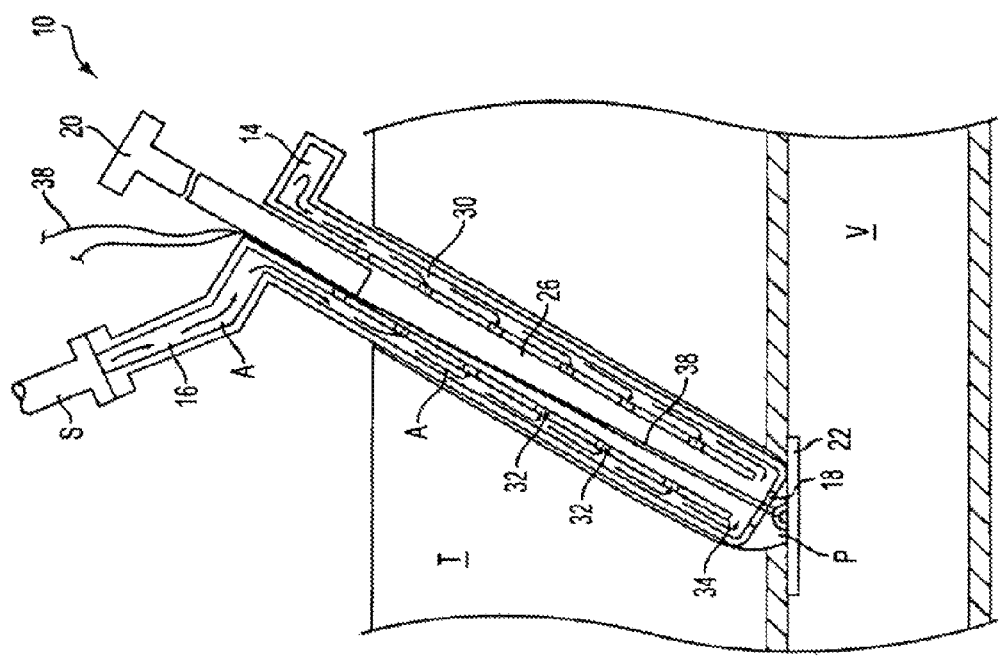
Figure 4E:
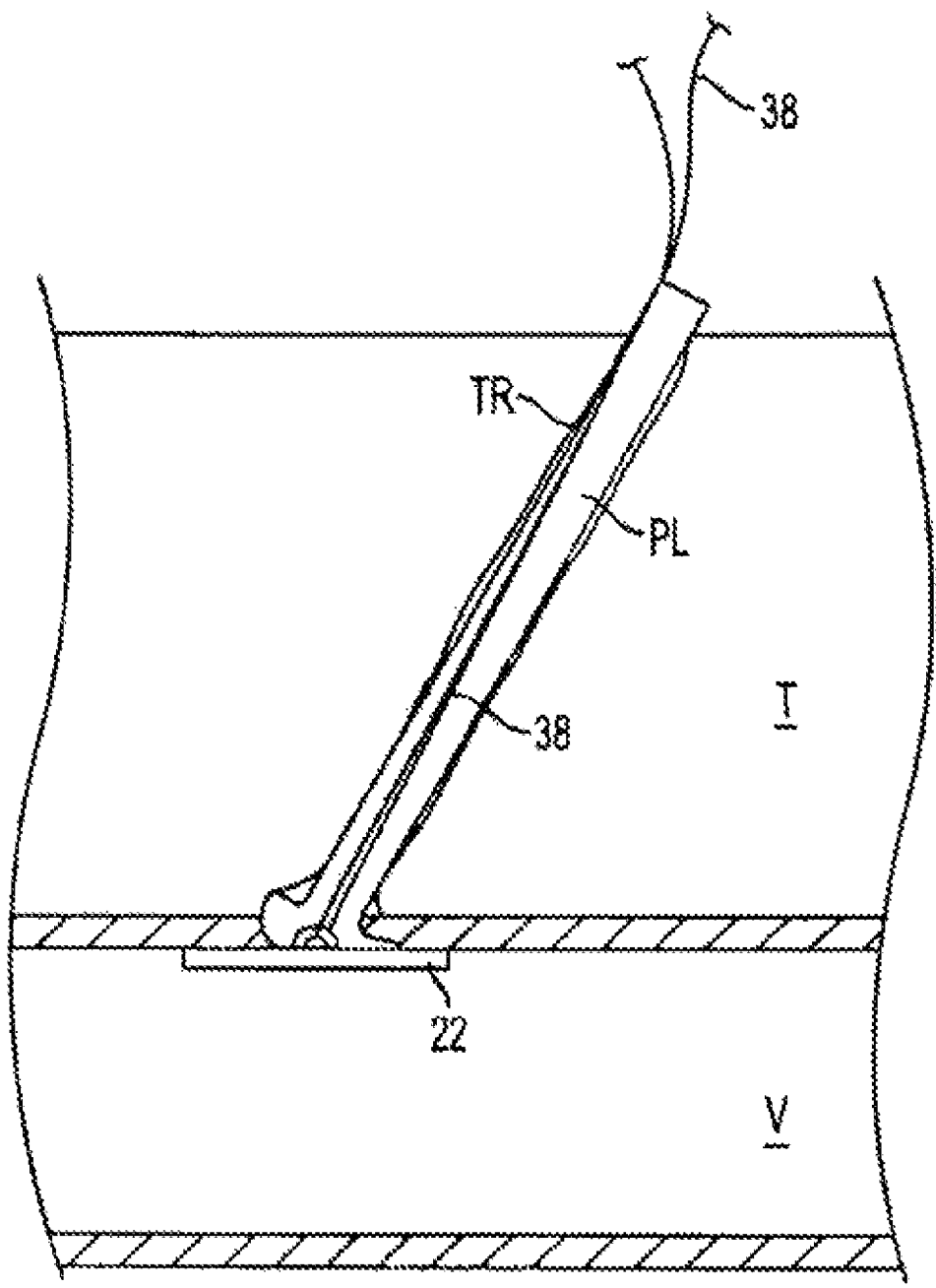

Referring now to FIG. 4, an exemplary method of using device 10 of the present invention is described. Housing 12 of device 10 optionally may comprise a cross-sectional area greater than that of puncture tract TR, and an introducer sheath (not shown) optionally may be used to introduce device 10 into the puncture tract. If housing 12 is sized such that its cross-sectional area does not exceed that of the puncture tract, the autologous plug formed within central lumen 26 and extruded into the puncture tract, as described hereinbelow, is expected to engage puncture tract TR, e.g. frictionally, via tissue rebound that decreases the diameter of the puncture tract after removal of device 10.

FIG. 4A illustrates device 10 disposed within puncture tract TR, for example, after the introducer sheath has been removed. Pledget 22 is disposed in the distal region of central lumen 26, and plunger 20 is disposed proximal to pledget 22 within central lumen 26. Device 10 is inserted into puncture tract TR and distally advanced therethrough until distal opening 18 is disposed just proximal of vessel V within puncture P. Positioning of device 10 may be confirmed by backbleed of blood B from injection port 16. Specifically, when distal opening 18 is advanced to a position just proximal of vessel V, blood B enters distal opening 18 and backbleeds through gap 34 and annular lumen 30, into manifold 14 and out of injection port 16.

Once device 10 is properly positioned just proximal of vessel V, plunger 20 is distally advanced. Because plunger 20 is disposed proximal pledget 22 within central lumen 26 and the diameter of shank 23 is only slightly less than the diameter of central lumen 26, distal advancement of plunger 20 also urges pledget 22 into vessel V. Preferably, plunger 20 contacts manifold 14 when pledget 22 has been completely advanced into vessel V. Because disk 42 of pledget 22 is elliptical, disk 42 will tend to align itself with its major axis parallel to the flow of blood, as shown in FIG. 4B.

Thereafter, plunger 20 is actuated in the proximal direction to draw blood B from vessel V into central lumen 26. Due to the presence of apertures 32 and gap 34, blood also may be drawn into annular lumen 30 and/or manifold 14. Any air within device 10 may escape therefrom through an air vent (not shown), and/or injection port 16.

Once central lumen 26 is filled with blood, a proximal force is applied to the proximal ends of thread 38 disposed outside of puncture tract TR to engage pledget 22 against the inner wall of vessel V, thereby sealing the puncture tract from the vessel and providing immediate hemostasis. Thereafter, source S of a blood congealing agent, such as thrombin, fibrin and/or human factor VIII, is coupled to injection port 16, and blood congealing agent A is injected into manifold 14. From manifold 14, agent A is introduced into blood present in annular lumen 30, and into central lumen 26 via apertures 32 and gap 34, where it initiates clotting of the blood therein. Due to the engagement of pledget 22 against the inner wall of vessel V, the blood congealing agent will not leak into vessel V.

After a period of time, the blood within central lumen 26 solidifies into autologous plug PL, with thread 38 embedded therein. In a preferred embodiment, autologous plug PL comprises a substantially cylindrical rod. Autologous plug PL then may be extruded from device 10 by actuation of plunger 20 and proximal retraction of device 10 from puncture tract TR.

Once autologous plug PL is extruded from device 10, it engages compliant tissue T surrounding puncture tract TR, which is expected to retract or rebound after removal of device 10, thereby establishing a compressive normal pressure between autologous plug PL and tissue T that reduces a risk of the plug becoming dislodged into vessel V. Any extraneous portion of autologous plug PL and thread 38 that proximally protrudes from puncture tract TR may be excised.

Figure 5A:
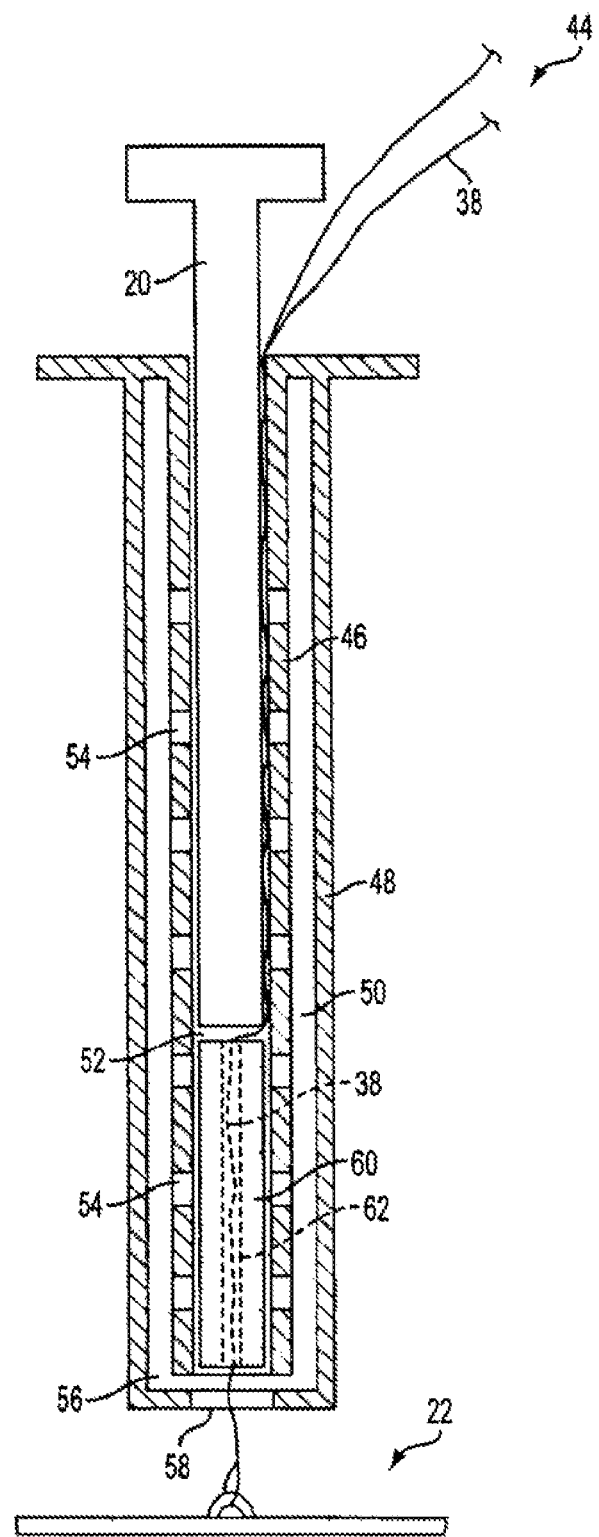

Referring now to FIG. 5A, an alternative embodiment of the present invention is described. Unlike the previous embodiment, device 44 omits manifold 14 and injection port 16, and retains plunger 20, pledget 22, and thread 38. Device 44 further comprises housing 52 having inner and outer tubes 46 and 48, which form annular lumen 50 that extends along the length of inner tube 46. Annular lumen 50 may be fluidically communicative with central lumen 52 via optional plurality of apertures 54, which may be disposed through and along the axial length of inner tube 46. Gap 56 is defined between the distal ends of inner and outer tubes 46 and 48.

Preferably, outer tube 48 is made from a transparent polymer. In use, this permits a medical practitioner to visually confirm proper placement of device 44 just proximal to vessel V. Specifically, when device 44 is advanced within puncture tract TR to a position just proximal of the vessel, blood backbleeds through opening 58 and gap 56 into annular lumen 50. If outer tube 48 is transparent, visual confirmation may be made. Air within annular lumen 50 may be evacuated through an air vent (not shown) in fluid communication with annular lumen 50.

The blood congealing agent of device 44 includes matrix 60 that is preferably biodegradable. Matrix 60 may comprise, for example, a gauze, a biologically compatible foam, and/or a spun fiber, such as a mass of a loosely spun fiber, e.g. polyglycolic acid. Matrix 60 promotes coagulation of blood upon contact and mixture therewith and optionally may be coated with, e.g., thrombin, fibrin and/or human factor VIII. Matrix 60 may comprise optional inner lumen 62 for disposition of thread 38 of pledget 22 through the matrix.

During delivery of device 44 into puncture tract TR, matrix 60 is disposed within central lumen 52 between plunger 20 and pledget 22. Once backbleed of blood into annular lumen 50 confirms that device 44 is positioned just proximal of vessel V, plunger 20 may be distally translated to advance pledget 22 into vessel V. This position, which may be indicated by a marker (not shown) on shaft 23 of plunger 20, corresponds to placement of matrix 60 just proximal of gap 56.

Thereafter, plunger 20 is proximally retracted to draw blood into device 44. Blood enters through opening 58 and saturates matrix 60 as it flows therethrough into the proximal portion of central lumen 52. Blood also may be drawn into annular lumen 50 via gap 56, and introduced into central lumen 52 via apertures 54, if present. Apertures 54 preferably are disposed along the length of inner tube 46, such that blood may evenly distribute along the length of central lumen 52, thereby evenly permeating matrix 60. Upon contact and mixture of the blood and the matrix, the blood congeals into an autologous plug that integrates matrix 60 therein. The resultant autologous plug is extruded from device 44 and disposed within puncture tract TR to compressively engage the surrounding tissue, thereby preventing leakage of blood therefrom.

Figure 5B:
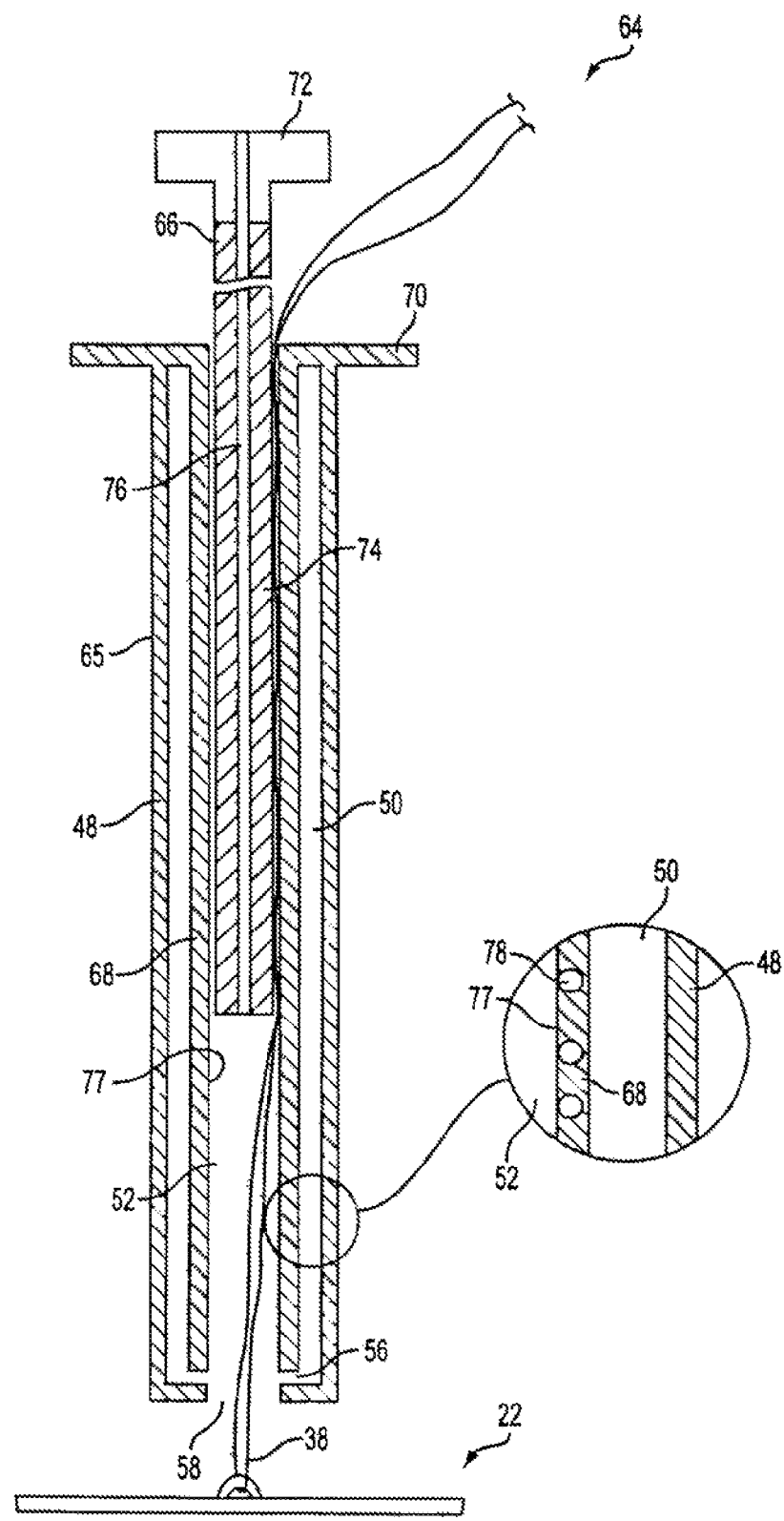

Referring now to FIG. 5B, an alternative embodiment of device 44 is described. Housing 65 of device 64 is similar to that of the previous embodiment, except that apertures 54 are omitted from inner tube 68 of the present embodiment. Device 64 also comprises plunger 66, pledget 22, and flange 70 that facilitates translation of housing 65 within puncture tract TR, and actuation of plunger 66 relative to housing 65. In the present embodiment, plunger 66 comprises injection port 72 disposed at the proximal end, shank 74 that is translatably disposed within central lumen 52, and injection lumen 76 disposed therethrough. Injection port 72 may comprise a coupling, such as a luer valve, that can be releasably joined to a source of blood congealing agent (not shown). Thus, instead of injecting blood congealing agent into a manifold as with device 10, device 64 permits injection directly into plunger 66, thereby eliminating apertures 32 from device 10 and reserving annular lumen 50 solely to provide visual confirmation of placement of device 64 relative to vessel V. It should be noted that injection lumen 76 also may be used as a thread lumen through which thread 38 attached to pledget 22 may be advanced (not shown).

In yet another alternative embodiment of the present invention, inner wall 77 of inner tube 68 may be pre-coated with a blood congealing agent, e.g., thrombin, fibrin and/or human factor VIII, or lined with a matrix that is preferably biodegradable (e.g., gauze or biologically compatible foam). This eliminates the need to separately introduce a fluid blood congealing agent into the blood isolated within central lumen 52, thereby eliminating the need for injection lumen 76 in plunger 66. Coagulation of blood further may be enhanced by contact with platinum wires 78, or convection and conduction of heat from thermo-resistive wires 78 disposed within inner tube 68, as shown in the inset of FIG. 5B. If thermo-resistive wires are provided, they may be proximally connected to a power source (not shown).

In a still further alternative embodiment of device 64, outer tube 48 may be omitted, thereby eliminating annular lumen 50, as well as gap 56. Shown in FIG. 5C, device 80 may be provided with only a single inner tube 68 having central lumen 52 in which shank 74 of plunger 66 may be translatably disposed. In this embodiment, central lumen 52 or injection lumen 76 of plunger 66 also may serve as a backbleed lumen through which blood may pass for visual confirmation of proper placement of device 80 proximate to vessel V. As discussed previously, injection lumen 76 further may be used as a thread lumen for disposition of thread 38 therethrough.

As with device 64, blood congealing agent may be introduced to the blood drawn into central lumen 52 by injection of the blood congealing agent into injection lumen 76, pre-coating or lining the central lumen with the blood congealing agent, e.g., thrombin, fibrin and/or human factor VIII, or exposing the blood to platinum or thermo-resistive wires. Additional techniques will be apparent to those of skill in the art.

As shown in FIGS. 5C-5E, the blood congealing agent also may include matrix 82 that is preferably biodegradable, and which is disposed within central lumen 52 between plunger 66 and pledget 22. Matrix 82 may comprise a gauze, a biologically compatible foam, and/or a spun fiber, e.g. a mass of loosely spun fiber, such as spun polyglycolic acid. Matrix 82 optionally may be coated with, e.g., thrombin, fibrin and/or human factor VIII. Upon contact and mixture with matrix 82, blood coagulates into an autologous plug, integrating the matrix and thread 38 therein.

As shown in FIG. 5D, matrix 82 preferably has a cross-section that incorporates plurality of longitudinal channels 84 and optional inner lumen 83 for disposition of thread 38 of pledget 22 therethrough. Channels 84 provide fluid communication between opening 86, disposed at the distal end of inner tube 68, and the proximal portion of central lumen 52. This permits blood to backbleed through matrix 82 and either injection lumen 76 or central lumen 52 to provide visual confirmation that device 80 is properly positioned just proximal to vessel V prior to actuation of plunger 66 to introduce pledget 22 within vessel V. Channels 84 also facilitate introduction and distribution of blood along the length of matrix 82, and into the proximal portion of central lumen 52. Preferably, matrix 82 expands to a substantially circular cross-section after mixture with the blood, thereby eliminating channels 84.

It will be evident to one of ordinary skill in the art that, while FIG. 5D illustrates a plurality of channels disposed along the circumference of matrix 82, channels 84 also may include other configurations, such as lumens 86 disposed through the longitudinal length of the matrix, as shown in FIG. 5E, or a combination thereof.

Figure 6:
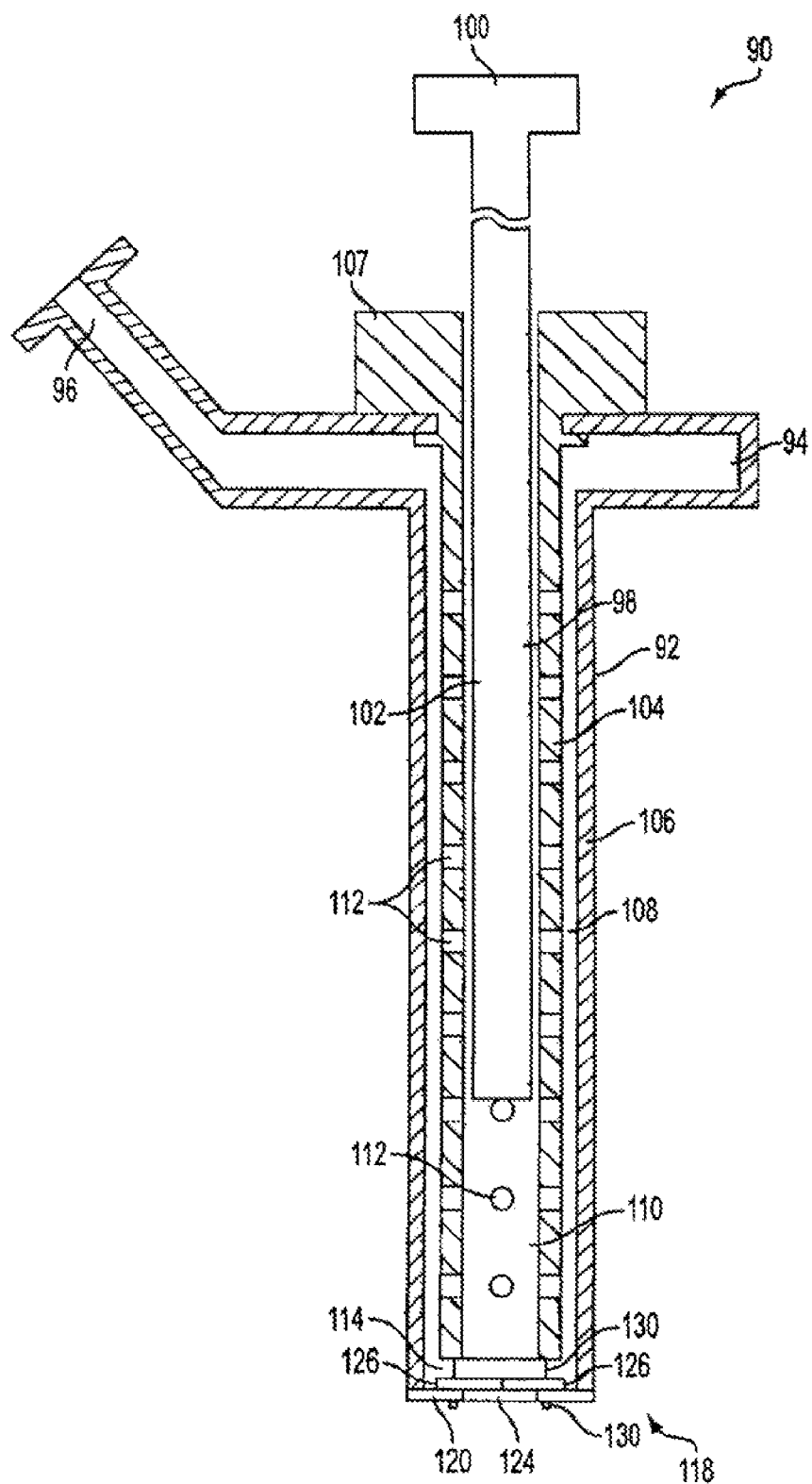
FIG. 6 is a schematic side-sectional view of another alternative embodiment of the apparatus of the present invention.

Referring now to FIG. 6, a still further alternative embodiment of the present invention is described. Like the embodiment of FIGS. 2 and 3, device 90 comprises housing 92 having manifold 94 and injection port 96, and plunger 98 having head 100 and shank 102 disposed for axial translation within housing 92. Housing 92 includes inner tube 104 and outer tube 106, wherein inner tube 104 is rotatable but not axially translatable relative to outer tube 106. Rotation of inner tube 104 may be facilitated by actuator 107 coupled thereto. Annular lumen 108 is formed between inner and outer tubes 104 and 106, and is in fluid communication with manifold 94 and injection port 96. Annular lumen 108 is in fluid communication with central lumen 110 via plurality of apertures 112, which is disposed through and along the axial length of inner tube 104. Gap 114 is defined between the distal ends of inner and outer tubes 104 and 106.

As in device 10, the diameter of central lumen 110 is designed to form an autologous plug therein, that engages tissue T when extruded into puncture tract TR. Shank 102 is slightly smaller than that of central lumen 110 and may be translated therein.

Instead of having a pledget to isolate blood from, and prevent leakage of blood congealing agent into, vessel V, device 90 includes iris closure 118 disposed at the distal end thereof. As shown in greater detail in FIGS. 7 and 8, iris closure 118 comprises iris plate 120 rigidly fixed to the distal end of outer tube 106, having tracks 122 and opening 124 therethrough. Iris closure 118 further comprises overlapping iris blades 126 that may be selectively actuated, as described hereinbelow, to expose or seal opening 124. Each iris blade 126 comprises distal bearing 128 and proximal bearing 130. Distal bearing 128 has a non-circular cross-sectional area, e.g., square, that is keyed to iris track 122. Distal bearing 128 also has end 131, e.g., a solder ball, having a diameter greater than the width of iris track 122 to prevent disengagement of distal bearing 128 from the iris track during actuation of iris closure 118. Proximal bearing 130 is configured to extend through gap 114 and into blind slots 132 disposed in the distal end of inner tube 104.

Figure 7A:
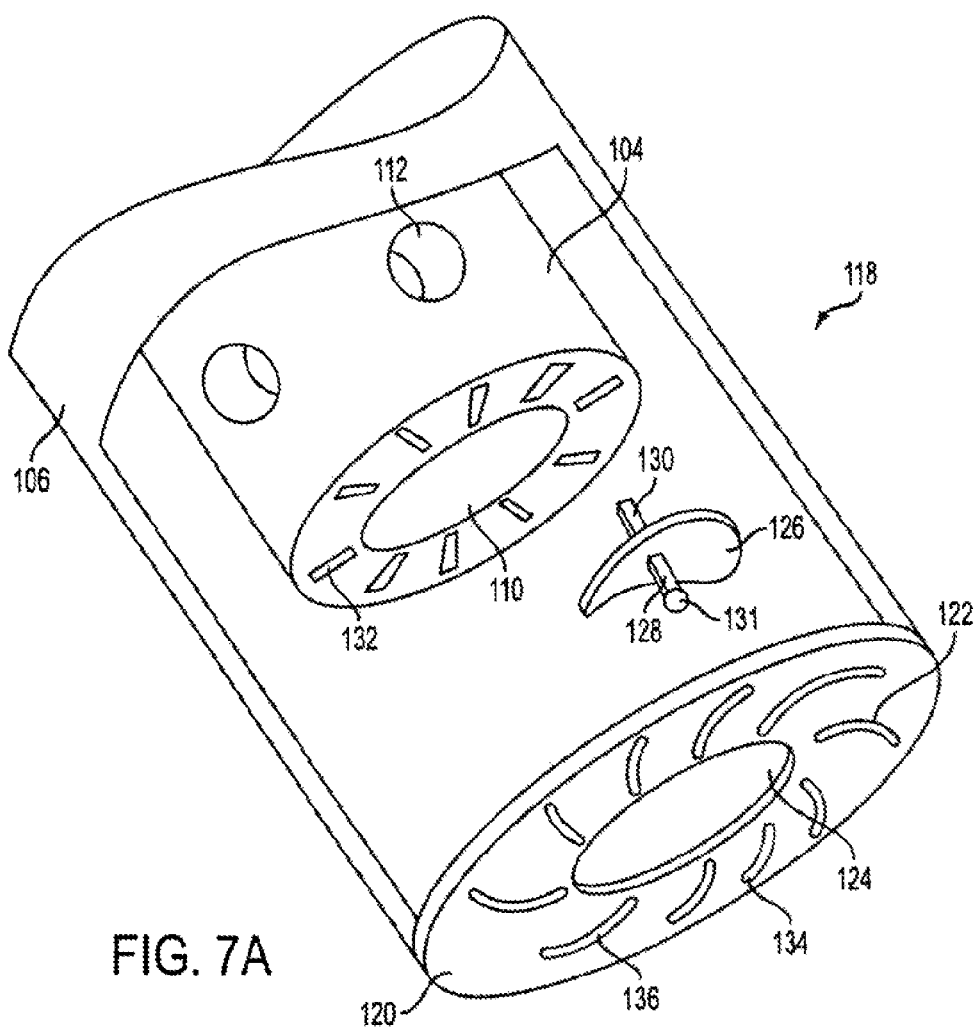
FIGS. 7A and 7B are, respectively, a schematic exploded perspective view and a schematic side-sectional view of an iris closure of the apparatus of FIG. 6.
Figure 8A:
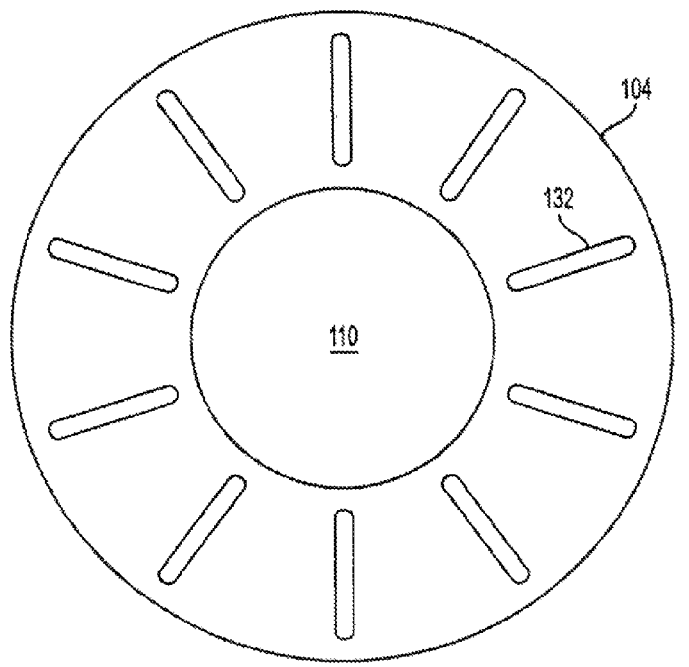
FIGS. 8A-8C are schematic plane views of an inner tube and the iris closure, respectively, of the apparatus of FIGS. 6 and 7.
Figure 8B:
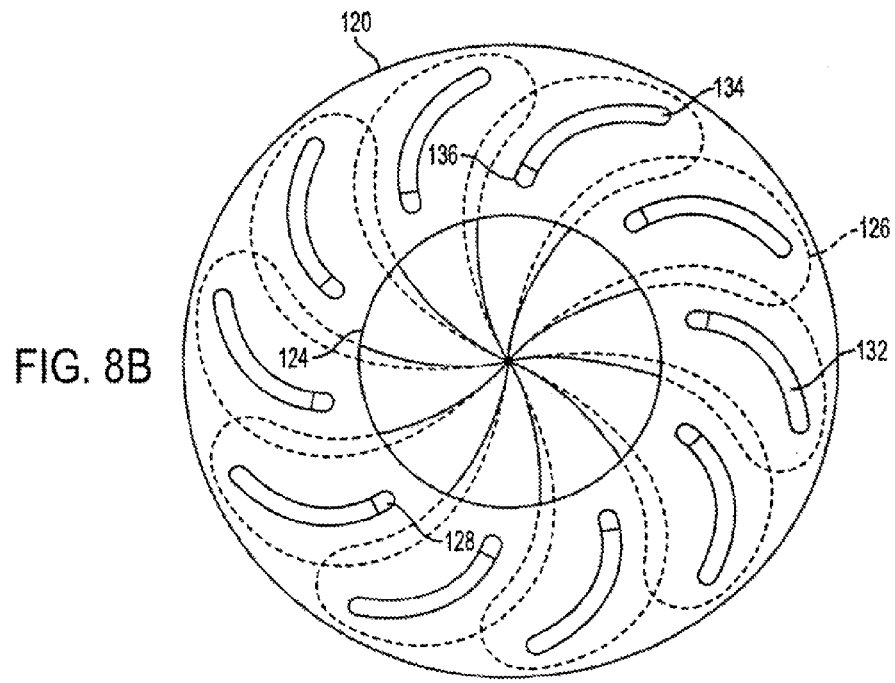
Figure 8C:
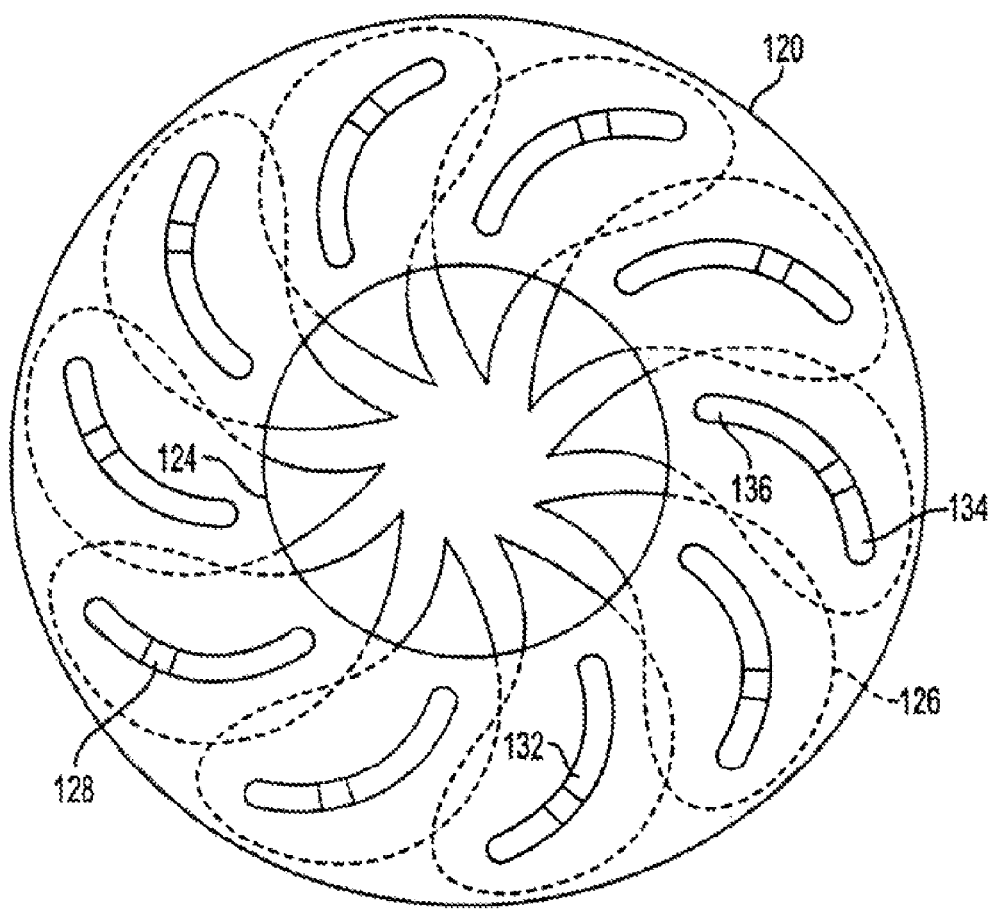

As shown in FIGS. 7A and 8A, slots 132 radially extend through the thickness of inner tube 104 without penetrating into central lumen 110 or annular lumen 108. As shown in FIGS. 7A, 8B and 8C, iris tracks 132 extend from opening 124 of iris plate 120 and curve along their respective lengths. The cross-sectional shapes of distal bearings 128 are keyed to iris tracks 122 so that actuation of distal bearings 128 along the iris tracks rotates distal bearings 128 along the curve of the iris tracks (see FIG. 8C). Since iris blades 126 are rigidly affixed to distal bearings 128, rotation of the distal bearings rotates iris blades 126 therewith, thereby exposing or sealing opening 124 depending on the direction of rotation of iris plate 120 relative to slots 132, or vice versa.

Figure 7B:
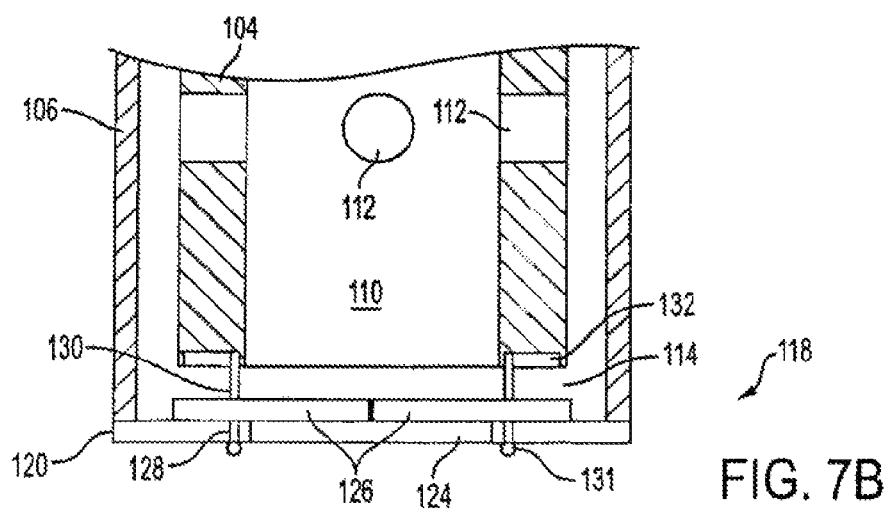

In operation, to expose opening 124 from its sealed configuration shown in FIGS. 7B and 8B, inner tube 104 is rotated, e.g., in the counter-clockwise direction relative to outer tube 106. This causes slots 132 engaged to proximal bearings 130 to impart a tangential force to each bearing 130. Since proximal bearings 130 are rigidly affixed to iris blades 126, the tangential forces imparted to bearings 130 force movement of iris blades 126 and distal bearings 128 along the curve of iris tracks 122. As illustrated in FIG. 8C, as distal bearings 128 travel therealong, iris blades 126 rotate with the curve of iris tracks 132, retracting the blades and exposing opening 124. Contemporaneously, proximal bearings 130 move along slots 132 in the outwardly radial direction. Rotation of inner tube 104 relative to outer tube 106 terminates when distal bearings 128 contact outer ends 134 of iris tracks 122. At this point, iris blades 126 have been completely retracted to expose opening 124.

To seal opening 124, inner tube 104 is rotated, e.g., in the clockwise direction relative to outer tube 106. This forces distal bearings 128 to move along the curve of iris tracks 122 in the inwardly radial direction towards opening 124, rotating iris blades 126 therewith to seal opening 124. When distal bearings 128 contact inner ends 136 of iris tracks 122, iris blades 126 have fully sealed opening 124.

While iris blades 126 are shown disposed proximal to iris plate 120 in FIGS. 6 and 7, it will be evident to one of ordinary skill in the art that iris blades 126 also may be disposed distal to iris plate 120, with minor design modifications to proximal bearings 130. Furthermore, it also will be evident that iris blades 126 may comprise numerous shapes other than the teardrop shape illustrated in FIGS. 7B, 8B and 8C.

Referring now to FIG. 9, an exemplary method of using device 90 is described. As discussed with reference to device 10, housing 92 of device 90 optionally may comprise a cross-sectional area greater than that of puncture tract TR. Accordingly, an introducer sheath (not shown) may be used to introduce device 90 into puncture tract TR. FIG. 9A illustrates device 90 in its delivery configuration after, for example, the introducer sheath has been removed, with iris blades 126 retracted to expose opening 124 within iris plate 120, and shank 102 of plunger 98 disposed within central lumen 110 just proximal to gap 114. This position may be indicated by a marker (not shown) disposed on shank 102, and permits blood to backbleed through gap 114 into annular lumen 108 to facilitate placement of device 90 relative to vessel V.

In this delivery configuration, device 90 is inserted into puncture tract TR and distally advanced therethrough until opening 124 is disposed just proximal to vessel V, as may be determined by observation of blood B exiting from injection port 96. In particular, when opening 124 is advanced to a position just proximal to vessel V, blood B enters opening 124 and backbleeds through gap 114 and annular lumen 108, into manifold 94 and out of injection port 96.

Figure 9B:
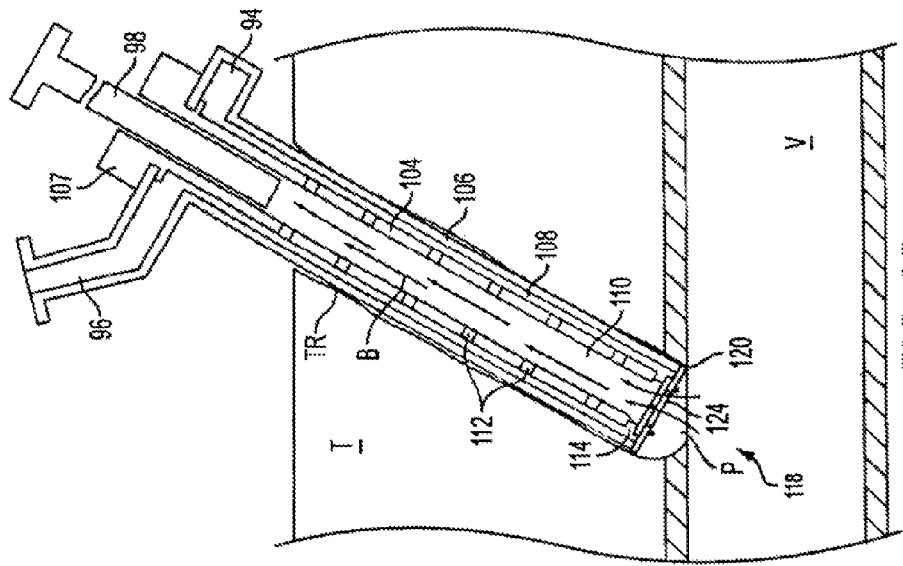
FIGS. 9A-9D are schematic side-sectional views describing an exemplary method of using the apparatus of FIGS. 6-8.
Figure 9A:
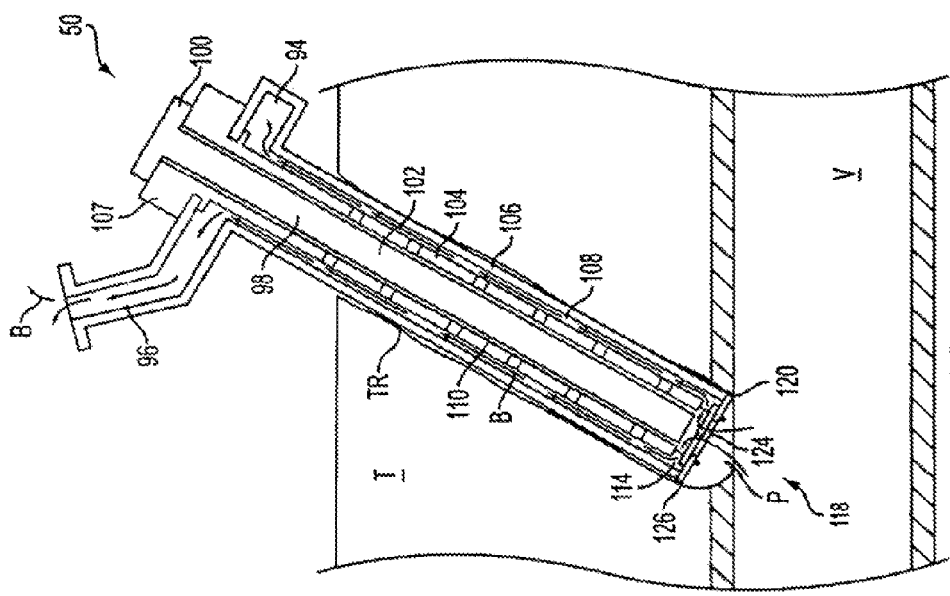
Figure 9D:
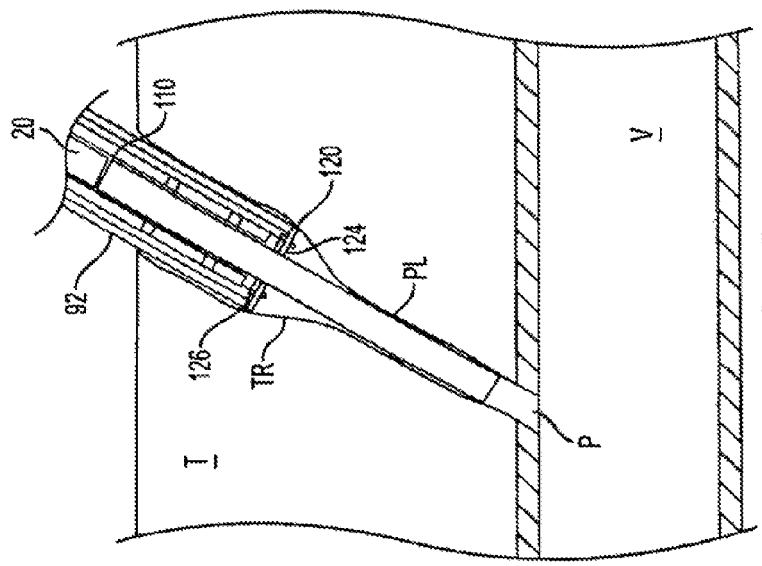
Figure 9C:
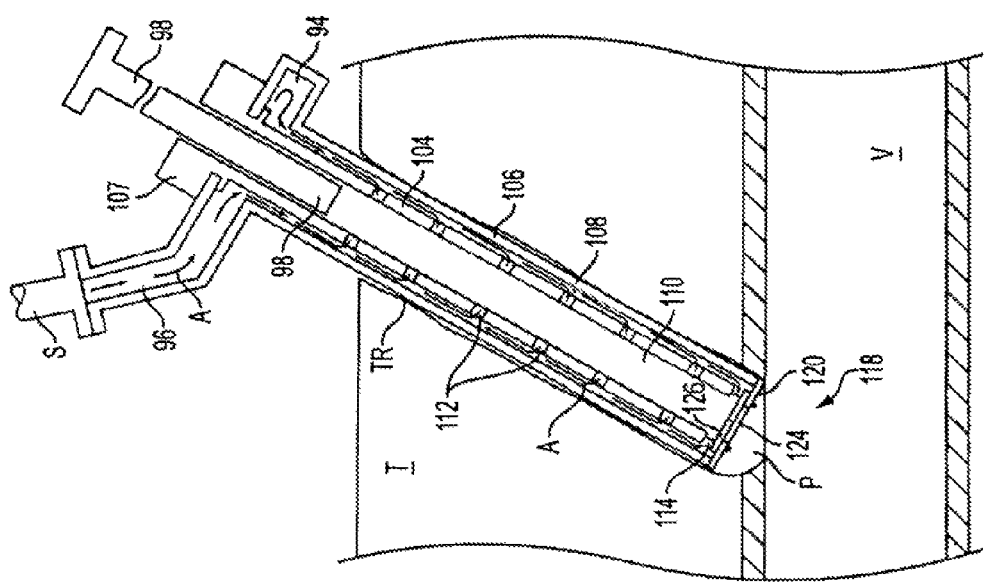

Once device 90 is properly positioned just proximal to vessel V, plunger 98 is actuated in the proximal direction to draw blood B from vessel V into central lumen 110, as seen in FIG. 9C. Due to the presence of apertures 112 and gap 114, blood also may be drawn into annular lumen 108 and/or manifold 94. Any air within device 90 may be expelled therefrom through an air vent (not shown) and/or injection port 96.

Once central lumen 110 is filled with blood B, actuator 107 may be used to rotate inner tube 104 relative to outer tube 106, actuating iris blades 126 to seal opening 124 in the manner discussed above.

Source S of blood congealing agent is coupled to injection port 96, and blood congealing agent A is injected into manifold 94. From manifold 94, blood congealing agent A mixes with blood present in annular lumen 108 and into central lumen 110, via apertures 112 and gap 114, initiating clotting of the blood. Since opening 124 is sealed, thereby isolating the blood within device 90, blood congealing agent A will not leak into vessel V. After a period of time, the blood within lumen 110 solidifies into autologous plug PL. Accordingly, in a preferred embodiment, autologous plug PL comprises a cylindrical rod.

Inner tube 104 then is rotated relative to outer tube 106 to expose opening 124 in the manner discussed above. Autologous plug PL is extruded from central lumen 110 by holding plunger 98 stationary as housing 92 is proximally retracted so that plunger 98 urges autologous plug PL out of lumen 110, as seen in FIG. 9D. Any blood contiguously coagulated with autologous plug PL, such as that potentially disposed within annular lumen 108, apertures 112, and gap 114, is expected to shear off when plug PL is extruded out of device 90.

Once autologous plug PL is extruded from device 90, it engages compliant tissue T surrounding puncture tract TR, which is expected to retract or rebound after removal of device 90, thereby establishing a compressive normal pressure between autologous plug PL and tissue T that reduces a risk of the plug becoming dislodged into vessel V. Any extraneous portion of autologous plug PL that proximally protrudes from puncture tract TR may be excised.

Figure 10A:
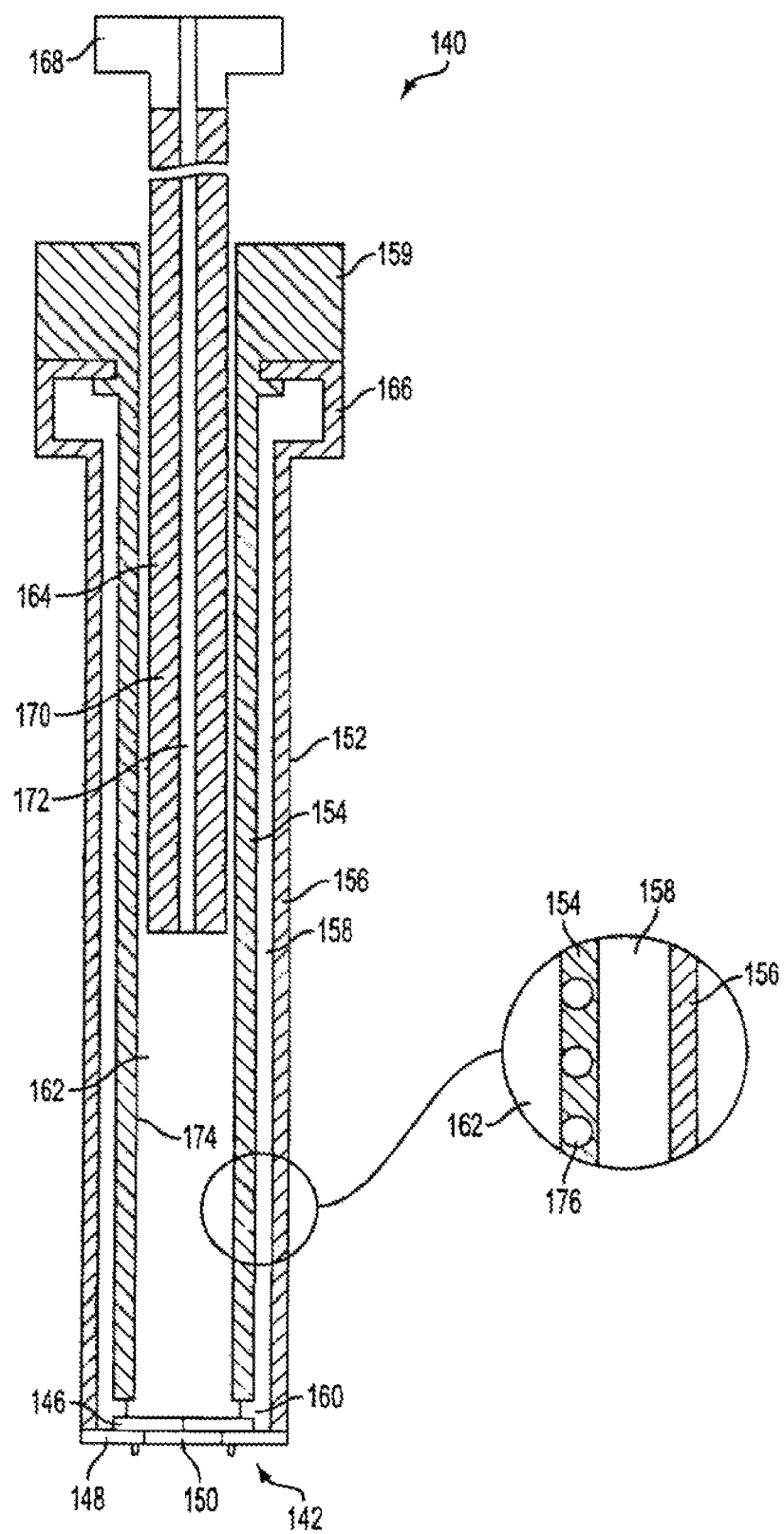
FIGS. 10A and 10B are schematic side-sectional views of alternative embodiments of the apparatus of FIGS. 6-9.

Referring now to FIG. 10A, a further is alternative embodiment of the present invention is described. Device 140 is similar to the preceding embodiment, except manifold 94 and apertures 112 have been omitted. Device 140 includes iris closure 142 having iris blades 146 operably engaged to iris plate 148, which includes opening 150 and a plurality of iris tracks similar to those described in FIGS. 7 and 8. Iris closure 142 is disposed on the distal end of housing 152 having inner tube 154, outer tube 156 which is rotatable but not axially translatable relative to inner tube 154, and annular lumen 158 disposed therebetween. Operated in the same manner as described previously with reference to FIGS. 7 and 8, rotation of inner tube 154, which may be facilitated by actuator 159 coupled thereto, actuates iris closure 142 to expose or seal opening 150, depending on the direction of rotation of inner tube 154 relative to outer tube 156. The distal ends of inner and outer tubes 154 and 156 define gap 160, which provides fluid communication among opening 150, annular lumen 158 and central lumen 162 of inner tube 154.

Preferably, outer tube 156 is made from a transparent polymer to facilitate visual confirmation of the advancement of device 140 to a position just proximal to vessel V in puncture tract TR. In use, when opening 150 is disposed just proximal to vessel V, blood backbleeds through opening 150 and gap 160 into annular lumen 158. Air within annular lumen 158 may be evacuated through an air vent (not shown) in fluid communication therewith.

Device 140 also comprises plunger 164 and flange 166 that facilitates insertion of housing 152 within puncture tract TR. In the present embodiment, plunger 164 comprises injection port 168 disposed at the proximal end, shank 170 that is configured to be translatably disposed within central lumen 162, and injection lumen 172 disposed therethrough. Injection port 168 may comprise a coupling, such as a luer valve, that can be releasably joined to a source of blood congealing agent (not shown). Accordingly, instead of injecting blood congealing agent into a manifold as in the preceding embodiment, device 140 permits injection directly into plunger 164, thereby eliminating apertures 112 from device 90 and reserving annular lumen 158 solely to provide visual confirmation of the disposition of device 140 just proximal to vessel V.

In an alternative embodiment of device 140, inner wall 174 may be pre-coated with a blood congealing agent, e.g., thrombin, fibrin and/or human factor VIII, or lined with a matrix (e.g., gauze, spun fiber or biologically compatible foam). This eliminates the need to introduce a blood congealing agent into the blood isolated within central lumen 162, thereby eliminating the need for injection lumen 172 in plunger 164. Coagulation of blood further may be enhanced by contact with platinum wires 176, or convection and conduction of heat from thermo-resistive wires 176 disposed within inner tube 154, as shown in the inset of FIG. 10A. Alternatively, central lumen 162 may be pre-filled with a matrix to promote coagulation of blood upon contact and mixture therewith, as described hereinabove with respect to FIGS. 5A and 5C-5E.

Figure 10B:
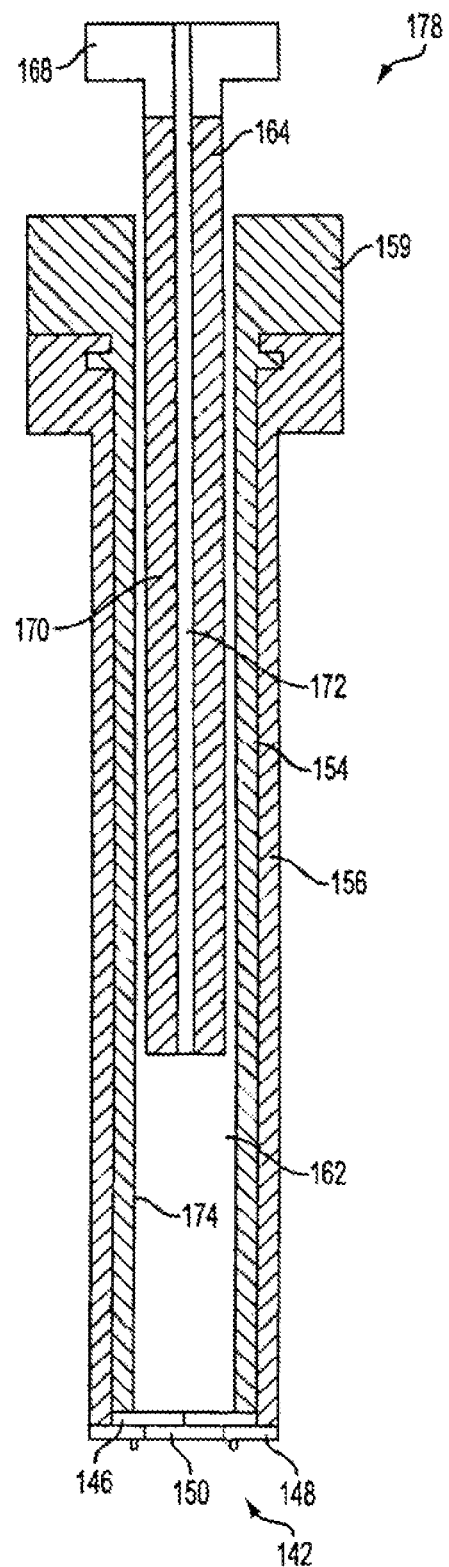

In an alternative embodiment of device 140, annular lumen 158 and gap 160 may be omitted. Shown in FIG. 10B, device 178 includes inner and outer tubes 154 and 156 adjacently disposed, and iris closure 142 operably coupled to the distal ends thereof. Central lumen 162 or injection lumen 172 of plunger 164 may serve as a backbleed lumen through which blood may pass for visual confirmation of proper placement of device 178 proximate vessel V.

As in device 140, blood congealing agent may be introduced to the blood drawn into central lumen 162 by injection of the blood congealing agent into injection lumen 172, pre-coating or lining the central lumen with the blood congealing agent, e.g., thrombin, fibrin, human factor VIII, and/or a matrix (e.g., gauze, spun fiber or biologically compatible foam), or exposing the blood to platinum or thermo-resistive wires. Alternatively, central lumen 162 may be pre-filled with a matrix to promote coagulation of blood upon contact and mixture therewith, as described hereinabove with respect to FIGS. 5A and 5C-5E.

Figure 11:
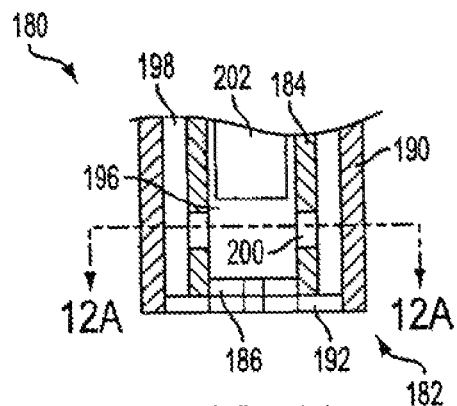
FIG. 11 is a schematic side-sectional view of a still further embodiment of the apparatus of the present invention.
Figure 12A:
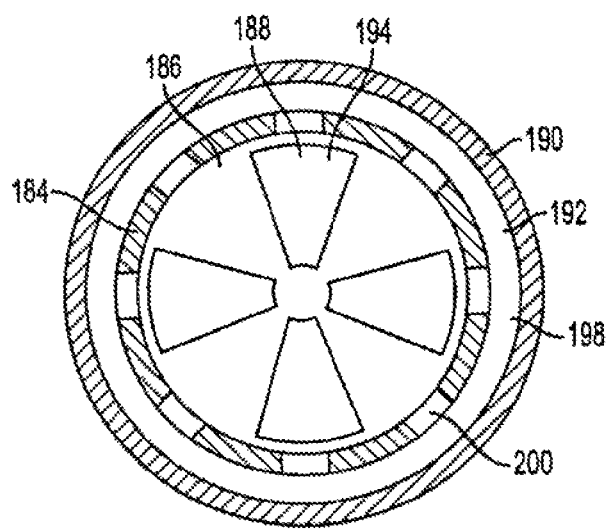
FIGS. 12A and 12B are schematic cross-sectional views of an alignment closure of the apparatus of FIG. 11.
Figure 12B:
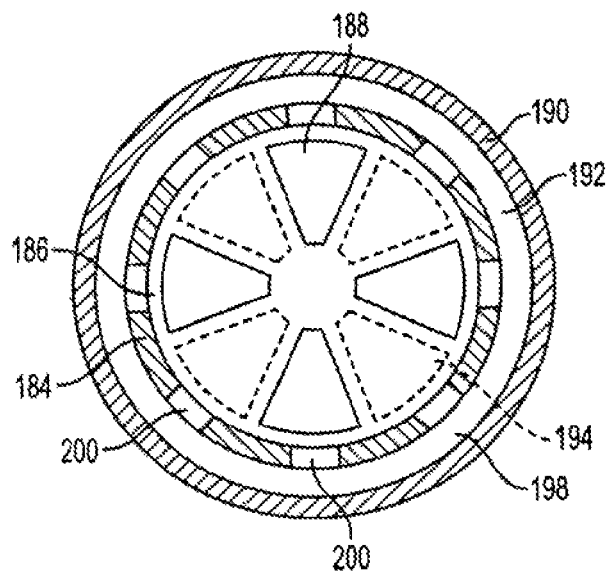

Referring now to FIG. 11, another embodiment of the apparatus of the present invention is described. Device 180 is similar to devices 90 and 140 respectively of FIGS. 6-8 and 10, except that the iris closures of those embodiments are replaced by alignment closure 182. Affixed to the distal end of inner tube 184 is proximal plate 186 having through-wall slots 188. Affixed to the distal end of outer tube 190 is distal plate 192 having through-wall slots 194 that have a shape identical to that of slots 188. When slots 188 and 194 are aligned, as shown in FIGS. 11 and 12A, blood may be drawn into central lumen 196 disposed through the length of inner tube 184, or an autologous plug may be extruded therethrough. When inner tube 184 is rotated relative to outer tube 190, distal and proximal plates 192 and 186 respectively obscure slots 188 and 194, as shown in FIG. 12B. In this configuration, blood is isolated within central lumen 196, and blood congealing agent may be supplied to the isolated blood to initiate clotting thereof.

Optional annular lumen 198 is defined by inner and outer tubes 184 and 190, and is in fluid communication with central lumen 196 via optional apertures 200 circumferentially disposed through inner tube 184 just proximal to proximal plate 186. To determine if device 180 has been properly positioned just proximal to vessel V, blood may backbleed through aligned slots 188 and 194 and apertures 200 into annular lumen 198. Accordingly, during delivery of device 180 into a puncture tract, the maximum distal position to which plunger 202 may be advanced within central lumen 196 is a position just proximal to apertures 200. This position may be indicated by a marker (not shown) disposed on plunger 202. As will be apparent to those of skill in the art, rather than having annular lumen 198 for backbleed indication, central lumen 196 of device 180 may serve as a backbleed lumen. Alternatively, a lumen may be provided through plunger 202 for backbleed indication and/or injection of a blood congealing agent, as described with respect to FIGS. 5B-5C and 10A-10B.

In operation, device 180 is inserted into puncture tract TR with slots 188 and 194 aligned, and plunger 202 disposed just proximal to apertures 200. Device 180 then is advanced to a position just proximal to vessel V. This position may be visually confirmed by observation of blood that backbleeds through slots 188 and 194 and, for example, apertures 200 into annular lumen 198 and/or out of a proximal injection port (not shown) in fluid communication with annular lumen 198. Plunger 202 then may be proximally retracted within central lumen 196 to draw blood therein from vessel V. Once central lumen 196 is filled, inner tube 184 is rotated relative to outer tube 190 to obscure slots 188 and 194, thereby isolating the drawn blood within device 180. Clotting of the blood may be initiated by introducing blood congealing agent into central lumen 196. Alternatively, the inner wall of inner tube 184 may be pre-coated with a blood congealing agent, e.g., thrombin, fibrin and/or human factor VIII, lined with a matrix (e.g., gauze, spun fiber or biologically compatible foam), or comprise platinum or thermo-resistive wires that are exposed to the blood therein. When the blood has solidified to form autologous plug PL, inner tube 184 is rotated relative to outer tube 190 to align slots 188 and 194. Plunger 202 is held stationary as device 180 is proximally retracted from puncture tract TR, thereby urging autologous plug PL from central lumen 196 through slots 188 and 194. Once disposed within puncture tract TR, the segments of the autologous plug that had been extruded through slots 188 and 194 are urged together due to the compressive pressure of tissue T surrounding the puncture tract. In this manner, puncture tract TR is sealed from leakage of blood.

Referring now to FIG. 13, yet another alternative embodiment of the present invention is described. Device 210 includes housing 212 having inner and outer tubes 214 and 216, which form annular lumen 218 therebetween. Device 210 also includes plunger 220 translatably disposed within central lumen 222, and membrane 224, which is preferably biodegradable. Membrane 224 is disposed over distal opening 226 of central lumen 222 and is releasably attached to inner wall 228 of inner tube 214 so that membrane 224 forms a sock within which is disposed blood congealing agent 230. Membrane 224 is preferably attached to inner wall 228 with a biodegradable adhesive or suture that permits the membrane to be sheared from inner wall 228 when an axial force is applied to blood congealing agent 230.

Membrane 224 is permeable to blood but impermeable to blood congealing agent 230, thereby permitting blood to be introduced into central lumen 222 and yet isolating the mixture of blood and blood congealing agent from vessel V. Selective permeability may be achieved, for example, by incorporating pores of a predetermined size within membrane 224. Thus, for example, the pores preferably have a cross-sectional dimension larger than the diameter of blood cells, but smaller than the diameter or cross-sectional dimension of the blood congealing agent, which also preferably may be provided with a predetermined size. Blood cells typically have a diameter of about 60 µm. A pore size greater than about 60 µm is therefore preferred.

Preferably, blood congealing agent 230 comprises a biodegradable matrix to promote coagulation of blood upon contact and mixture therewith, as described hereinabove with respect to FIGS. 5A and 5C-5E. Alternatively, blood congealing agent 230 also may comprise powder of a blood congealing substance, such as polyglycolic acid, fibrin, thrombin and/or human factor VIII.

Outer tube 216 preferably is made from a transparent polymer to permit observation of blood that backbleeds into annular lumen 218 when device 210 is disposed just proximal to vessel V. This provides a medical practitioner with visual confirmation of proper placement of device 210 within puncture tract TR. Optionally, inner tube 214 also may comprise apertures 232 disposed along the length thereof. Apertures 232 provide fluid communication between annular lumen 218 and central lumen 222. During proximal retraction of plunger 220, blood may be drawn through apertures 232 and blood permeable membrane 224 into central lumen 222 to more evenly distribute the blood along the length of central lumen 222 and to evenly permeate blood congealing agent 230.

In operation, device 210 is introduced into puncture tract TR with plunger 220 disposed within central lumen 222 just proximal to blood congealing agent 230. Device 210 is distally translated along the puncture tract until backbleeding, e.g. through annular lumen 218, indicates that the device is properly positioned just proximal to vessel V. Plunger 220 then is actuated in the proximal direction to draw blood into central lumen 222 through membrane 224, covering distal opening 226, as well as apertures 232, if present. Contact and mixture with blood congealing agent 230 coagulates the blood into an autologous plug, integrating blood congealing agent 230 and membrane 224 therein. When plunger 220 is translated in the distal direction to extrude the formed autologous plug from central lumen 222, the distal force transmitted to the adhesive or suture binding membrane 224 to inner wall 228 shears membrane 224 therefrom. Disposed within puncture tract TR, the autologous plug engages tissue T surrounding the puncture tract to prevent blood leakage from vessel V.

In an alternative embodiment of device 210, outer tube 216 and apertures 232 may be omitted, thereby eliminating annular lumen 218. For backbleed indication to facilitate visual confirmation of the placement of the present device just proximal to vessel V, plunger 220 may be provided with an injection lumen like that described with respect to FIGS. 5B-5C and 10A-10B.

While preferred illustrative embodiments of the invention are described above, it will be apparent to one skilled in the art that various changes and modifications may be made therein without departing from the invention. For example, shorter autologous plugs may be formed that only cover a portion of the length of the puncture tract. Furthermore, various blood congealing agents described hereinabove and known to those in the art may be used in combination in a single embodiment. The appended claims are intended to cover all such changes and modifications that fall within the true spirit and scope of the invention.

What is claimed is:

1. A device for sealing a puncture tract by forming and extruding an autologous plug within the puncture tract, the device comprising:
    a housing having a lumen adapted to mix a volume of blood with a blood congealing agent to form the autologous plug;
    a selectively closable iris cooperating with a distal opening of the lumen of the housing, the selectively closable iris is configured to be inserted into the puncture tract and to isolate the mixture of the volume of blood and the blood congealing agent from the vessel during formation of the autologous plug within the lumen; and
    a plunger disposed for translation within the lumen to extrude the autologous plug formed within the lumen.

2. The device of claim 1, wherein the housing comprises a second lumen to facilitate placement of a distal end of the device.

3. The device of claim 1, wherein the housing comprises an inner tube forming the lumen and an outer tube substantially extending along an axial length of the inner tube, wherein relative rotation between the inner tube and the outer tube moves the selectively closable iris between a first position, wherein the distal opening of the lumen is exposed, and a second position, wherein the distal opening of the lumen is substantially sealed by the selectively closable iris.

4. The device of claim 3, wherein the inner tube is axially fixed relative to the outer tube.

5. The device of claim 1, wherein the autologous plug formed in the lumen has a length and a form factor that causes the autologous plug to engage tissue surrounding the puncture tract after ejection by the plunger into the puncture tract.

6. The device of claim 1, wherein the selectively closable iris a plate having a plurality of tracks and an opening disposed therethrough, and a plurality of blades operably engaged to the plurality of tracks.

7. The device of claim 1, wherein the blood congealing agent is pre-disposed within the lumen.

8. The device of claim 7, wherein the blood congealing agent is coated onto an interior surface of the lumen.

9. The device of claim 1, wherein the blood congealing agent is introduced into the lumen subsequent to actuation of the selectively closable iris.

10. The device of claim 9, wherein the blood congealing agent comprises a platinum wire.

11. The device of claim 10, wherein the blood congealing agent comprises a thermo-resistive wire.

12. The device of claim 1, wherein the blood congealing agent is chosen from the group consisting of thrombin, fibrin, human factor VIII, and combinations thereof.

13. The device of claim 1, wherein the blood congealing agent comprises a matrix.

14. The device of claim 13, wherein the matrix is chosen from the group consisting of gauze, biocompatible foam, and spun fiber.

15. The device of claim 13, wherein the matrix is biodegradable.

16. The device of claim 13, wherein the matrix has a cross-sectional geometry at least partially defining a plurality of longitudinal channels and at least one inner lumen disposed therethrough.

17. A device for sealing a puncture tract by forming and extruding an autologous plug within the puncture tract, the device comprising:
- a housing having a lumen adapted to mix a volume of blood with a blood congealing agent;
- a membrane cooperating with the lumen of the housing that is permeable to blood and impermeable to the blood congealing agent, the membrane is configured to be inserted into the puncture tract and to isolate the mixture of the volume of blood and the blood congealing agent from the vessel during formation of the autologous plug; and
- a plunger disposed for translation within the lumen to extrude the autologous plug formed within the lumen.

18. A device for sealing a puncture tract by forming and extruding an autologous plug within the puncture tract, the device comprising:
- a housing including an inner tube forming a central lumen adapted to mix a volume of blood with a blood congealing agent, and an outer tube forming an annular lumen between the inner tube and the outer tube, the annular lumen extending substantially along an axial length of the inner tube;
- a closure element cooperating with a distal opening of the central lumen, the closure element is configured to be inserted into the puncture tract and to isolate the mixture of the volume of blood and the blood congealing agent from the vessel during formation of the autologous plug within the central lumen, wherein relative rotation between the inner tube and the outer tube moves the closure element between a first position, wherein the distal opening of the central lumen is exposed, and a second position, wherein the distal opening of the central lumen is substantially sealed by the closure element; and
- a plunger disposed for translation within the central lumen to extrude the autologous plug formed within the lumen.

19. The device of claim 18, wherein the annular lumen is in fluid communication with the central lumen via a plurality of apertures disposed through and along the axial length of the inner tube.

20. The device of claim 18, wherein the closure element comprises first and second plates, each of the first and second plates having a plurality of through-wall slots, the first and second plates being relatively rotatable to selectively align the pluralities of through-wall slots.

* * * * *